(12) United States Patent
Rubinsky et al.

(10) Patent No.: US 7,053,063 B2
(45) Date of Patent: *May 30, 2006

(54) CONTROLLED ELECTROPORATION AND MASS TRANSFER ACROSS CELL MEMBRANES IN TISSUE

(75) Inventors: Boris Rubinsky, Milpitas, CA (US); Yong Huang, Milpitas, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/139,012

(22) Filed: May 26, 2005

(65) Prior Publication Data

US 2005/0282284 A1    Dec. 22, 2005

Related U.S. Application Data

(63) Continuation-in-part of application No. 10/079,940, filed on Feb. 19, 2002, now Pat. No. 6,927,049, which is a continuation-in-part of application No. 09/618,951, filed on Jul. 19, 2000, now Pat. No. 6,482,619, which is a continuation-in-part of application No. 09/358,510, filed on Jul. 21, 1999, now Pat. No. 6,300,108.

(51) Int. Cl.
*A61K 31/713* (2006.01)

(52) U.S. Cl. ............... 514/44; 435/461; 435/285.2

(58) Field of Classification Search ............... None
See application file for complete search history.

(56) References Cited

U.S. PATENT DOCUMENTS

| | | | |
|---|---|---|---|
| 4,810,963 A | 3/1989 | Blake-Coleman et al. | |
| 5,098,843 A | 3/1992 | Calvin | |
| 5,134,070 A | 7/1992 | Casnig | |
| 5,173,158 A | 12/1992 | Schmukler | |
| 5,283,194 A | 2/1994 | Schmukler | |
| 5,991,697 A | 11/1999 | Nelson et al. | |
| 6,300,108 B1 * | 10/2001 | Rubinsky et al. | 435/173.6 |
| 6,482,619 B1 * | 11/2002 | Rubinsky et al. | 435/173.7 |
| 6,613,211 B1 | 9/2003 | McCormick et al. | |

FOREIGN PATENT DOCUMENTS

WO    WO 01/07583    2/2001

OTHER PUBLICATIONS

Andreason, G.L., *J. Tiss. Cult. Meth.*, 15:56-62 (1993).
Barber, *Advances in Biomedical Engineering*, J.E.W. W.Beneken and V. Thevenin (eds) IOS Press pp. 165-173 (1993).
Cook et al., *IEEE Transactions on Biomedical Engineering*, 41(6):713-722 (Aug. 1994).
Duraiswami et al., *Engineering and Analysis with Boundary Elements*, 22:13-31 (1998).
Duraiswami et al., *Chemical Engineering Science*, 32(13):2185-2196 (1997).
Duraiswami et al., *Bounary Element Technology XII*, pp. 226-237 (1997).
Fox et al., Sampling Conductivity Images Via MCMC, Mathematics Department, Auckland University, New Zealand (May 1997).
Gencer et al., *IEEE Transactions on Biomedical Engineering*, 43(2):139-149 (Feb. 1996).
Gilbert et al., *Biochimica et Biophysica Act*, 1334:9-14 (1997).
Griffiths et al., *Phys. Med. Biol.*, 3(10):1465-1476 (Oct. 1989).
Griffiths et al., *IEEE Transactions on Biomedical Engineering*, 42:948-954 (1995).
Griffiths et al., *Phys. Med. Biol.*, 32(11):1435-1444 (1987).
Glidewell et al., *Biomed Sci Instrum*, 29:251-257 (1993).
Gumerov et al., *13th International Conference on Boundary Element Technology*, BETECH, Las Vegas, Nevada (Jun. 1999).
Hapala, I., *Critical Reviews in Biotechnology*, 17:105-122 (1997).
Heller et al., *Advanced Drug Delivery Reviews*, 35:119-129 (1999).
Ho et al., *Critical Reviews in Biotechnology*, 16:349-362 (1996).
Holder et al., *Proceedings of the X. International Conference on Electrical Bioimpedance*, pp. 479-482 (1997).
Hughes et al., *Physiol. Meas.*, 15:A199-A209 (1994).
Jaroszeski et al., *Advanced Drug Delivery Reviews*, 35:131-137 (1999).
Liu et al., *Clin. Phys. Physiol. Meas.*, 13(Suppl. A):197-200 (1992).
Lorquin, P.G., *Molecular Biotechnology*, 7:5-35 (1997).
Lundqvist et al., *Proc. Natl. Acad. Sci. USA*, 95:10356-10360 (1998).
Mir et al., *Cancerology*, 313(III):613-618 (1991).
Narayan et al., *J. Urol.*, 148:1600-1604 (1992).
Neumann et al., *EMBO J*, 7:841-845 (1982).

(Continued)

Primary Examiner—James Ketter
(74) Attorney, Agent, or Firm—Karl Bozicevic; Bozicevic, Field & Francis LLP

(57) ABSTRACT

Electroporation is performed in a controlled manner in individual and multiple biological cells present in biological tissue by monitoring the electrical impedance, defined herein as the ratio of current to voltage in the electroporation cell. The impedance detects the onset of electroporation in the biological cell(s), and this information is used to control the intensity and duration of the voltage to assure that electroporation has occurred without destroying the cell(s). This is applicable to electroporation in general.

20 Claims, 20 Drawing Sheets

OTHER PUBLICATIONS

Schmuckler, "Impedance Spectroscopy of biological cells," *Engineering in Medicine and Biology Society*, 1994. Engineering Advances: New Opportunities for Biomedical Engineers., Proceedings of the 16th Annual Internal Conference of the IEEE.

Sharma et al., *Biophysical Journal*, vol. 71:3229-3241 (1996).

Weaver, J.C., *Journal of Cellular Biochemistry*, 51:426-435 (1993).

Blad et al., "Impedance spectra of tumour tissue in comparison with normal tissue; a possible clinical application for electrical impedance tomography" *Physiol Meas* 17:A105-A115 (1996).

* cited by examiner

Calculated electrical field and estimated electroporated area from
i. 25 ii. 50 iii. 75 percent of tissue exposed.
(1000V/0V; 2.5cm tissue width; 350V/cm threshold in white; no flux exterior)

|   | Percent of tissue exposed to electrode | | | |
|---|---|---|---|---|
| Applied voltage ratio [V/cm] | 25 | 50 | 75 | 100 |
| 200 | 1.4 | 1.7 | 1.8 | 3.2(0.8) *** |
| 250 | - | 2.5 | - | 12.1(0.3) ** |
| 300 | 2.1(1.5) ** | 2.5(0.3) ** | 9.2(0.1) ** | 14.2(2.5) ***** |
| 350 | 1.5 | 9.2 | 16.7 | 19.2(1.2) ** |
| 400 | 6.3(0.3) ** | 9.1(2.2) ** | 17.0(0.7) *** | 22.7(1.4) **** |
| 450 | - | 12.7(4.3) ** | - | 33.05(5.1) **** |
| 500 | 7.9 | 13.8 | 16.7 | 34.8(6.5) *** |

Average percent drop and standard deviation in overall resistance 10-15 seconds after electroporation pulse

Figure 7

Experimental summary of two electrode system

| Field [V/cm] | sample size | area [cm] | length [cm] | Is drop | ~15-30s drop | R [Ohm] | ρ [Ohm cm] | CT [S/m] |
|---|---|---|---|---|---|---|---|---|
| 200 | 2x2x3 | 0.6 | 2.5 | -20% | -9% | 4250 | 1020 | 0.10 |
| 300 | 2.5x2x.3 | 0.6 | 2.5 | -29% | -13% | 5000 | 1200 | 0.08 |
| 400 | 2.5x1.8x.2 | 0.4 | 2.5 | -45% | -21% | 6955 | 1001 | 0.10 |
| 500 | 2.4x1.7x.2 | 0.3 | 2.4 | -77% | -40% | 5380 | 762 | 0.13 |

Figure 8

Potential Distribution and general schematic for first example. (7cm tissue; 1.1mm electrodes; 8mm apart edge-to-edge; no flux exterior; 800V/0V)

Selected steps for first example a: Electric field distribution [V/cm] b: Conductivity map [S/m] The light area indicates electroporated tissue. c: Generated image.

Selected steps for second example a: Electric field distribution [V/cm] b: Conductivity map. The light area indicates electroporated tissue. [S/m] c: Generated image.

Selected steps for third example
a: Electric field distribution [V/cm] b: Conductivity map [S/m] The light area indicates electroporated tissue. c: Generated image.

Baseline example (10cm tissue; Four 1mm electrodes; 10mm apart center-to-center; no flux exterior; 1300V/0V) a: Updated conductivity map [S/m] b: Generated image.

Effect of domain size on generated image a: 25cm b: 35cm c: 50cm.

Effect of inner region conductivity on generated image a: 0.19 S/m b: 0.20 S/m c: 0.21 S/m.

Effect of number of imaging electrodes on generated image a: 16 b: 24 c: 32.

Effect of the initial radius of the inner region on generated image a: 6mm b: 8mm c: 10mm.

Effect of the number of elements used to define the inner region on generated image a: 18 b: 20 c: 22.

CONTROLLED ELECTROPORATION AND MASS TRANSFER ACROSS CELL MEMBRANES IN TISSUE

CROSS-REFERENCE

This application is a continuation-in-part of application Ser. No. 10/079,940, filed Feb. 19, 2002, now U.S. Pat. No. 6,927,049, which is a continuation-in-part of application Ser. No. 09/618,951, filed Jul. 19, 2000, now U.S. Pat. No. 6,482,619, which is a continuation-in-part of application Ser. No. 09/358,510, filed Jul. 21, 1999, now U.S. Pat. No. 6,300,108 issued Oct. 9, 2001, all of which are incorporated herein by reference and to which are claimed priority under 35 USC §120.

FIELD OF THE INVENTION

This invention resides in the fields of electroporation and mass transfer across cell membranes and more specifically to electroporation of cells in tissue.

BACKGROUND OF THE INVENTION

Electroporation is a technique that is used for introducing chemical species into biological cells, and is performed by exposing the cells to an electric potential that traverses the cell membrane. While its mechanism is not fully understood, electroporation is believed to involve the breakdown of the cell membrane lipid bilayer leading to the formation of transient or permanent pores in the membrane that permit the chemical species to enter the cell by diffusion. The electric potential is typically applied in pulses, and whether the pore formation is reversible or irreversible depends on such parameters as the amplitude, length, shape and repetition rate of the pulses, in addition to the type and development stage of the cell. As a method of introducing chemical species into cells, electroporation offers numerous advantages: it is simple to use; it can be used to treat whole populations of cells simultaneously; it can be used to introduce essentially any macromolecule into a cell; it can be used with a wide variety of primary or established cell lines and is particularly effective with certain cell lines; and it can be used on both prokaryotic and eukaryotic cells without major modifications or adaptations to cell type and origin. Electroporation is currently used on cells in suspension or in culture, as well as cells in tissues and organs.

Electroporation is currently performed by placing one or more cells, in suspension or in tissue, between two electrodes connected to a generator that emits pulses of a high-voltage electric field. The pore formation, or permeabilization, of the membrane occurs at the cell poles, which are the sites on the cell membranes that directly face the electrodes and thus the sites at which the transmembrane potential is highest. Unfortunately, the degree of permeabilization occurring in electroporation varies with the cell type and also varies among cells in a given population. Furthermore, since the procedure is performed in large populations of cells whose properties vary among the individual cells in the population, the electroporation conditions can only be selected to address the average qualities of the cell population; the procedure as currently practiced cannot be adapted to the specific characteristics of individual cells. Of particular concern is that under certain conditions, electroporation can induce irreversible pore formation and cell death. A high electric field, for example, may thus produce an increase in transfection efficiency in one portion of a cell population while causing cell death in another. A further problem with known methods of electroporation is that the efficiency of transfection by electroporation can at times be low. In the case of DNA, for example, a large amount of DNA is needed in the surrounding medium to achieve effective transformation of the cell.

Many of the problems identified above are a consequence of the fact that the process of electroporation in both individual cells and tissues cannot be controlled in real time. There are no means at present to ascertain in real time when a cell enters a state of electroporation. As a result, the outcome of an electroporation protocol can only be determined through the eventual consequences of the mass transfer process and its effect on the cell. These occur long after the mass transfer under electroporation has taken place. These and other deficiencies of current methods of electroporation are addressed by the present invention.

Also relevant to the present invention are current techniques for the study and control of mass transfer across cell membranes. Knowledge of mass transfer across cell membranes in nature, both in cells that are functioning normally and in diseased cells, is valuable in the study of certain diseases. In addition, the ability to modify and control mass transfer across cell membranes is a useful tool in conducting research and therapy in modern biotechnology and medicine. The introduction or removal of chemical species such as DNA or proteins from the cell to control the function, physiology, or behavior of the cell provides valuable information regarding both normal and abnormal physiological processes of the cell.

The most common method of effecting and studying mass transfer across a cell membrane is to place the cell in contact with a solution that contains the compound that is to be transported across the membrane, either with or without electroporation. This bulk transfer method does not permit precise control or measurement of the mass transfer across the membrane. The composition of the solution at specific sites is not known and is variable. In addition, when an electric field is present, the local field intensity will vary from one point to another. Furthermore, the surface of the cell that is exposed to the solution is not well defined. Cell surface areas vary among cells in a given population, and this leads to significant differences among the cells in the amount of mass transfer. For these reasons, the amount of mass transfer achieved by bulk transfer processes is not uniform among cells, and the actual amount transferred for any particular cell cannot be determined.

Attempts made so far to overcome the limitations of bulk transfer techniques include techniques for treating individual cells that include either the mechanical injection (microinjection) of chemical compounds through the cell membrane or electroporation with microelectrodes. In injection techniques, the membrane is penetrated with a needle to deliver a chemical agent, localizing the application of the chemical agent to a small region close to the point of injection. This requires manipulation of the cell with the human hand, a technique that is difficult to perform, labor-intensive, and not readily reproducible. Electroporation with microelectrodes suffers these problems as well as the lack of any means to detect the onset of electroporation in an individual cell. These problems are likewise addressed by the present invention.

As indicted above electroporation is used in biotechnology and medicine for introducing molecules that normally do not penetrate the cell membrane into the cell. This is done by applying electrical pulses across the cell membrane. For a certain range of amplitudes and times of application the electrical pulses can reversible permeabilize the cell membrane, while pulses below that range have no effect on the membrane and above that range induce irreversible permeabilization. In general electroporation was a trial and error procedure, with the optimal electrical pulse parameters for electroporation chosen by evaluating the biological outcome of the procedure on the cell. In our earlier patents such as U.S. Pat. No. 6,482,619 we showed that cell permeabilization by electroporation can be detected by measuring electrical currents through the cells—under the assumption that the permeabilization of the cell membrane will also cause a change in the ionic flux through the cell. This in turn can be used to detect, control and optimize electroporation protocols, in real time. Using a single cell microelectromechanical chip we have provided examples of how this procedure can be used with single cells. Exactly the same concept can be also applied for controlling electroporation in a multitude of cells through experiments with cells in a confluent cell layer and with cells in tissues and such is exemplified below.

SUMMARY OF THE INVENTION

The present invention arises in part from the discovery that the onset and extent of electroporation in a biological cell and a group of cells in tissue can be correlated to changes in the electrical impedance (which term is used herein to mean the ratio of current to voltage) of a conductive medium that includes the biological cell or tissue. An increase in the current-to-voltage ratio across a group of biological cells occurs when membranes of the cells become permeable due to pore formation. Likewise, a decrease in the current-to-voltage ratio through a flowing conductive fluid occurs when the fluid draws biological cells into the region between the electrodes in a flow-through electric cell. Thus, by monitoring the impedance of the biological cells in a tissue, one can detect the point in time in which pore formation of the cells on average occurs, as well as the relative degree of cell membrane permeability due to the pore formation. This information can then be used to establish that on average the cells of the tissue have in fact undergone electroporation, or to control the electroporation process by governing the selection of the voltage magnitude. The invention provides the simultaneous electroporation of multitudes of cells, since it provides a direct indication of the actual occurrence of electroporation and an indication of the degree of electroporation averaged over the multitude. The discovery is likewise useful in the electroporation of biological tissue (masses of biological cells with contiguous membranes) for the same reasons.

The benefits of this process include a high level of control over the onset and degree of electroporation, together with a more detailed knowledge of the occurrence and degree of permeability created in particular cell masses. When applied to cells this process assures that on average, the cells of the tissue are indeed rendered permeable and are indeed transformed by the introduction of chemical species and this can be observed and measured in real time. The process also offers the ability to increase the efficiency of electroporation by avoiding variations in the electrical environment that would destroy some cells while having an insufficient effect on others.

In some of its more specific embodiments, the present invention involves the use of an electrical cell in which a an extracted tissue sample can be placed and that contains a barrier that directs the electric current flow and hence the ion flow through a flow path that passes through the tissue sample while permitting substantially no electric current to bypass the tissue sample. In some of these embodiments, the invention involves the use of an apparatus containing two liquid-retaining chambers separated by a barrier that is substantially impermeable to an electric current. The barrier contains an opening that is smaller than the tissue sample such that the tissue sample once lodged in the opening will plug or close the opening. To achieve electroporation, the tissue sample is secured over the opening by mechanical or chemical means, preferably in a reversible manner so that the tissue sample can later be removed without damage to the tissue. Once the tissue sample is secured over the opening, a voltage is imposed between the two chambers and across the tissue sample residing in the opening. The passage of current between the chambers is thus restricted to a path passing through the opening and hence through the tissue sample. By monitoring the current-voltage relation in the electric cell, the onset of electroporation is detected and the degree of pore formation is controlled, to both assure that electroporation is, on average, occurring and to prevent, on average, excessive pore formation and cell death. The user is thus afforded a highly precise knowledge and control of the condition of and the flux across an average of the cells of the tissue.

In another series of embodiments, this invention is useful in the diffusive transport of chemical species into or out of cells of a tissue. In these embodiments, the tissue sample is again divided into two chambers separated by a barrier, and the tissue sample is lodged across an opening in the barrier in such a manner that the passage of liquid around the tissue sample from one chamber to the other is substantially prevented. A liquid solution of the species to be introduced into cells of the tissue is placed in one or both of the chambers. The concentration of the species in the solution differs from that in cells of the tissue (either higher or lower, depending on whether one seeks to introduce or remove the species from the cells), or the concentration in one chamber differs from that in the other chamber.

In preferred methods of applying this invention to diffusive transport, the solutions in the two chambers differ in concentration such that the driving force for the diffusive transport is between the two chambers themselves rather than between the chambers and the interior of cells of the tissue. Knowledge and controlled monitoring of the concentrations in each of the two chambers on a periodic or continuous basis as the diffusion proceeds, together with the precise knowledge of the dimensions of the opening, enables the user to precisely observe and control, on average, the rate and amount of the species that enters an average cell of the tissue. The diffusion time can be controlled by imposing stepwise changes in the concentrations in either or both of the chambers, thereby imposing or removing the concentration differential. An application of particular interest is the combination of this type of diffusive transport of a chemical species with controlled electroporation as described in the preceding paragraph.

Each of the various embodiments of this invention may be used with different sizes of tissue samples. The apparatus described above can be adapted for use with different sizes of tissue samples by arranging the barrier such that the current or diffusive transport will be restricted to a flow path that passes through all of the cells of the sample while preventing bypass around the cells of the sample.

A further application of the concepts of this invention is the electroporation of biological cells suspended in a flowing liquid. Electrodes are placed in fixed positions in the flow channel, and a voltage is imposed between the electrodes while current passing between the electrodes is monitored.

Biological cells entering the region between the electrodes will lower the current, the impedance serving as an indication of the presence of one or more cells in the region, and optionally also as a signal to initiate the application of a higher voltage sufficient to achieve electroporation.

Among the advantages that this invention offers relative to the prior art are the ability to treat tissue samples individually and to adapt the treatment conditions to the needs of individual tissue samples. In embodiments where voltage is applied, the monitoring of the impedance affords the user knowledge of the presence or absence of pores and shows the progress of the pore formation and whether irreversible pore formation that might lead to cell death has occurred. An advantage of the barrier-and-opening apparatus is its highly efficient use of electrical energy by virtue of its restriction of the current to a current flow path passing through the opening. A still further advantage is the ability of the apparatus and method to be integrated into an automated system whereby the condition of each tissue sample is monitored by instrumentation and individual tissue sample are lodged in the opening and then removed at times governed by the monitored conditions.

An aspect of the invention is a method whereby cells of tissue are electroporated while measuring and/or observing changes in electrical impedance in real time and noting increases as a beginning to electroporation and adjusting current to avoid as much as possible irreversible cellular damage.

A feature of the invention is that the magnitude of electrical current during electroporation of cells of tissue becomes dependent on the degree of electroporation of the cells so that current is adjusted within a range predetermined to obtain a desired degree of electroporation minimizing cellular damage.

Another feature of the invention is that measuring (in real time) current through a circuit gives a measurement dependent on the overall and average degree of electroporation that the cells in the tissue between the electrodes experience.

Another aspect of the invention is that precise electrical resistance of the tissue is calculated from cross-time voltage measurement with probe electrodes and cross-current measurement with the circuit attached to electroporation electrodes.

These and further features, advantages and objects of the invention will be better understood from the description that follows.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 7 is a chart of percent of tissue exposed to electrode vs. Applied voltage ratio.

FIG. 8 is a chart of data of a two electrode system.

DETAILED DESCRIPTION OF THE INVENTION

Figure 1:
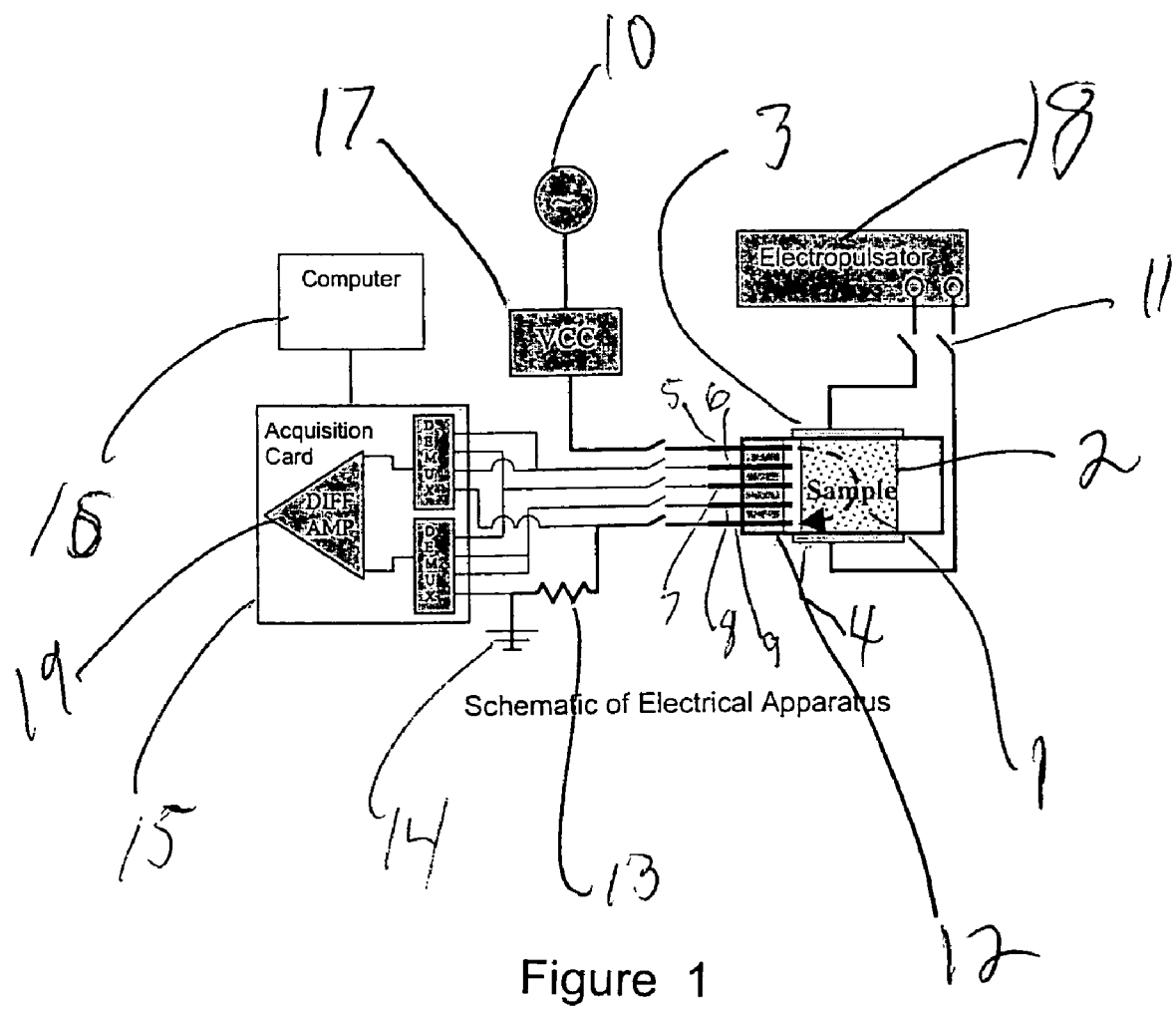
FIG. 1 is a schematic view of an electroporation system.

Before the present methods, treatments and devices are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a pulse" includes a plurality of such pulses and reference to "the sample" includes reference to one or more samples and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Single Cell Layer Electrode System

In an electroporation protocol cells are: a) grown on a substrate, b) separated from the substrate through trypsinization, c) introduced into a cell suspension in which they float d) than the cell suspension is electroporated without real time control between electrodes, with pulses determined through a trial and error procedure, e) after electroporation the cells are seeded on a cell growth substrate and f) the cells are grown to determine through biochemical markers if the electroporation was successful. This is a six step procedure. Cell electroporation can be detected in real time for individual cells as well as a multitude of cells in a layer. This basic concept is applied here for an electroporation procedure that detects and controls electroporation in real time in a multitude of cells grown on a substrate. This facilitates electroporation with real time control of a layer of cells on the substrate directly without the need to trypsinize the cells, electroporate in a suspension and than seeding for further growth on the substrate.

The apparatus used for electroporation of a multitude of cells in a single layer is shown in FIG. 1. The basis of the apparatus is the use of the electrodes 3 and 4 monitored by electrons 5–9. The Example described here may use a commercial membrane insert (Millicel-PCF, # PIHP03050 Millipore, USA), which has a porous membrane with pores of 0.4 microns and a porosity of 10%. Other types of porous inserts can be used as well.

In a typical electroporation procedure for cells grown in a cell layer, the cells are grown to a desire confluence on the porous insert as described by the Millipore company instructions. During an electroporation protocol, the cell insert is introduced between the electrodes 3 and 4, as shown in FIG. 1. An electrolyte is introduced to generate good contact between the cell layer and the electrodes 3 and 4. Then electrical pulses are applied to the adherent cells through the two electroporation electrodes 3 and 4; which are connected to the power amplifier 18. Measuring the electrical current through this electrical circuit is dependent on the overall and average degree of electroporation that the cells 1 in the sample 1. Once the cells in the sample 1 are electroporated, there shall be increased electrical current flow through the cells and the magnitude of the electrical current becomes dependent on the degree of electroporation of the adherent cells. This cross-cell electrical current can be measured with the amplifier 19 and can be used to monitor the process of electroporation of the cell membranes. In addition to the current measurement, the five inserted probe electrodes 5, 6, 7, 8 and 9 are used to precisely measure the voltage drop across the cell layer of the sample 1 during the electroporation process, without the artifacts induced by the build-up of the ionic layer across the electroporation electrodes 3 and 4. The probe electrodes 5–9 connected to the high amplifier 19 may be used to cancel out the voltage drops at the electroporate electrodes 3 and 4 interfaces and provide accurate readings on the voltage across the cell layer of the sample 1. Precise electrical resistance of the cell layer in the sample 1 is thus calculated from cross-cell-layer voltage measurement with the probe electrodes 5–9. The resistance measurement reveals the degree of electroporation of the cell layer of the sample 1 since cell membrane resistance is directly dependent on the extent of membrane electroporation. In addition to monitoring the electroporation, the electrical current measurement as well as membrane resistance measurement can be used as feedback for fine-tuning of electroporation pulses to achieve highly controlled electroporation of the cells in the sample 1.

Tissue Electroporation Four Electrode System

In tissue electroporation, which is done either in vitro or in vivo, the tissue which one desires to electroporate is introduced between two electrodes 3 and 4 of FIG. 1 and the electrical pulses applied so that the cells will become electroporated. There may be no real time information on the degree or type of electroporation. The basic concept that cell electroporation can be detected in real time for individual cells as well as a multitude of cells in a layer as well as cells in tissue can be used to detect electroporation in real time in tissue.

In a typical electroporation procedure for tissue the tissue sample 1 is placed between the two electrodes 3 and 4 as shown in FIG. 1, for in vitro electroporation. An electrolyte is introduced to generate good contact between the tissue of sample 1 and the electrodes 3 and 4. Then electrical pulses are applied to the tissue through the two electroporation electrodes 3 and 4; which are connected to the electropulsator 18. Measuring the electrical current through this electrical circuit may be made dependent on the overall and average degree of electroporation that the cells in the tissue sample between the electrodes experience.

Once the cells are electroporated, there shall be increased electrical current flow through the cells and the magnitude of the electrical current becomes dependent on the degree of electroporation of the cells in tissue. This cross-cell electrical current can be measured with via the electrodes 5–9 and can be used to monitor the process of electroporation of the cell membranes. The two probe electrodes 5–9 connected to the amplifier 19 can be used to cancel out the voltage drops at the electroporate electrodes interfaces and provide accurate readings on the voltage across the tissue.

Precise electrical resistance of the tissue is thus calculated from cross-tissue voltage measurement with the probe electrodes 5–9 and cross-current measurement. The resistance measurement reveals the degree of electroporation of the cells in tissue sample 1 since cell membrane resistance is directly dependent on the extent of membrane electroporation. In addition to monitoring the electroporation, the electrical current measurement as well as membrane resistance measurement can be used as feedback for fine-tuning of electroporation pulses to achieve highly controlled electroporation of the cells in tissue in the sample 1.

EXAMPLE

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Materials

Cells—Two types of cells were examined: Mouse skin fibroblasts (NIH 3T3 cell line) and primary skeletal satellite cells. Satellite cells were isolated and expanded. The cells were plated on membrane inserts (Millicel-PCF, # PIHP03050 Millipore, USA) and incubated for 5 days in culture medium (DMEM, 10% Fetal calf serum, 1% L-glutamine, antibiotics, Biological industries, Bet Haeemek, Israel) in 6 wells plates until desired confluence was achieved.

Tissue—Liver was obtained from Spraque Dewley rats (250–350 gr), and used within 10 minutes from resection. The liver was removed from the anesthetized rat and sliced with a scalpel to a thickness ranging from 1 mm to 4 mm. Then a disk of liver was obtained by pressing a sharp circular tube onto the sample to trim the excess tissue. The resulting sample can then placed in a device as shown in FIG. 1 for measurement. For negative controls livers can used and should be kept prior to resection in a refrigerator at 4° C.

Electrical Parameters Study

Cells—Inserts with adherent layers of cells can be placed into the configuration shown in FIG. 1, medium can be collected, cells washed with PBS (phosphate buffered solution) and additional PBS can be introduced to ensure good contact between the electrodes and both sides of the confluent cell layer. Confluency test can be performed, and after which a series of electroporation pulses can be given and the electrical data recorded.

Tissue—The tissue layer can be placed between the measurement electrodes. Then PBS should be added to ensure good contact between the electrodes and the tissue.

Transgene Expression

To assess the efficacy of transgene delivery and expression, 2 plasmids: CMV-GFP and MSV-MyoD may be used. The GFP reporter gene may be introduced to cultured fibroblasts or to satellite cells to assess the efficiency of gene delivery. MSV-MyoD may be introduced to cultured fibroblasts to test gene-based myogenic conversion.

Inserts may be placed into the system in FIG. 1, medium may be collected, cells washed with PBS, and 1 ml PBS containing plasmid DNA (1 µg/ml) introduced to the cell layer. 6 ml PBS may be placed at the electroporation system chamber. After which a series of electroporation pulses can be given. After the electroporation, PBS can be discarded and replaced by fresh culture medium. Cells can then incubated (5% $CO^2$ incubator, 37° C.) for 3 days.

Transgene Expression Gene delivery efficiency may be determined, 3 days after electroporation by the extent of the expression of GFP reporter gene, with a fluorescent microscope. Treated fibroblasts or satellite cells can be trypsinized (trypsin EDTA solution, Biological industries, Bet Haeemek, Israel) and centrifugated at 1800 rpm for 10 minutes at RT. The pellet can be suspended in cold PBS with glucose (2.5 gr/L), and cytospinned at 500 rpm for 15 minutes on glass microscope slides. GFP expression may be observed under green filter fluorescence microscope.

The MyoD-treated fibroblasts may be incubated for six hours in medium DMEM with 10% FCS, then, shifted to differentiation (low serum) medium (DMEM medium supplemented with 2% FCS) for three days.

Electroporation Electrical Measurement Results

A typical three steps electrical pulse may be used to study the process of electroporation in cell layers and tissue samples. It consists of three steps. The first pulse is a low amplitude pulse that cannot produce electroporation and is used to probe the typical electrical impedance of the cells or tissue prior to electroporation. The second pulse was varied in amplitude until a change in the electrical impedance of the cells was detected to determine the occurrence of electroporation. The occurrence of electroporation results in a decrease in the electrical impedance of the cells—while electrical pulses which do not produce electroporation will not affect the electrical impedance of the cells. It should be noted that while the polarity of the pulse was chosen to be negative, relative to the electrode in which the plasmids were introduced from electrophoretic considerations to facilitate insertion of the charged plasmids into the cells. The third electrical pulse has the same amplitude as the first. The impedance measured during the third pulse may be used to determine if the electroporation was reversible or not. The effect of several three pulse steps, separated by various intervals of time may studied.

The above Examples demonstrate the potential for electrical impedance tomography (EIT) to monitor electroporation by incorporating the conductivity change of a single cell during electroporation into an electrical model representing the whole tissue. However, cells in tissue inside the body are surrounded by extracellular conductive fluid and we now show that the bulk properties of tissue are measurably affected by electroporation. This is done here by quantifying the normalized change in conductivity of rat liver tissue ex vivo as a function of an exposed electric field. Parameters such as pulse duration, number of pulses, and time from sacrifice are investigated as a function of an applied electric field. The results show that the cells of the tissue are controllably electropermeabilized, and that the conductivity of tissue increases substantially and predictably and shows that electrical impedance tomography (BIT) can produce an image of the electroporated area.

Experimental Methods

These ex vivo experiments are designed to quantify the normalized conductivity change of tissue due to sets of electrical pulses, typical to in vivo EGT and ECT. In general, 6–12 pulses are applied at a frequency of 1 Hz, combining higher electric fields with short pulse lengths (100 µs) for ECT and lower fields with longer pulses (>1 ms) for gene therapy. The normalized conductivity change is measured as opposed to the absolute values of tissue resistivity due to the large variation in tissue properties from animal to animal.

Experimental Setup

The system used is a simple single-frequency bio-impedance measurement system for rectangular tissue slices. The experimental apparatus is shown in FIG. 1. For each experiment, tissue sample 1 was placed onto a glass microscope slide 2 surrounded by electrodes 3 and 4. The configuration consisted of two separate sets of electrodes: one to administer the electroporation pulses (electrodes 3 and 4) and the other set 5, 6, 7, 8 and 9 for bioimpedance measurement. There is one switch 10 to disengage the measurement electrodes 5–9 and another switch 11 to engage the electroporation electrodes to prevent the systems from interfering with each other.

Tissue Electroporation

The electroporation system of FIG. 1 is designed to supply eight square wave pulses up to 500V cm$^{-1}$ across the width of the tissue. Two parallel stainless steel plate electrodes were placed along the width of the slide to apply the electric pulses. The electroporation pulses were generated using a Jouan PS-15 square wave electropulsator (Jouan, St Herblain, France). To convert from desired electric field, E, to applied voltage, V, for this device, the desired field is multiplied by the electrode spacing, s, (in this case 2.54 cm), by 110% to account for losses, and finally by ⅔ (because the original electrodes that came with this system were 1.5 cm apart). For example, the voltage is set to 372V to apply a 250V/cm pulse. An oscilloscope was attached to the system to verify delivery of the electric pulses.

$$110\% \frac{2}{3} E * s = V$$

Measurement of Tissue Conductivity Change

To quantify the impedance change of tissue sample 1 undergoing electroporation, the system of FIG. 1 was designed analogous to bioimpedance measuring devices that separate the injecting electrodes from the recording electrodes. There are five 0.7 mm-wide square stainless steel rods 5–9 equally spaced at 4.5 mm, center-to-center, attached to one end of the slide with epoxy. A sinusoidal current is injected from the first electrode 5 through the sample 1 and out the last electrode 9. Its path is depicted as a heavy solid line 12 in FIG. 1. These outer electrodes 5 and 9 act as a permanent source/sink injection pair and the three electrodes 6,7, and 8 in-between are used for measurements.

This three-electrode configuration enables one to verify their experimental measurements through three different electrode combinations. The first and last electrodes are not used for measurements because the contact resistance would cause uncertainty. One injecting pair and one measuring pair (at any given time) is common in bioimpedance measurement systems and has been shown to dramatically improve results over single pair systems, which inject and measure through the same electrodes.

The current through the system of FIG. 1 was determined by measuring the voltage drop across a 2 kOhm resistor 13 located between the last electrode 9 and ground 14. Constant current is used as opposed to constant voltage to minimize contact impedance at the source and sink electrodes. To generate this current, a function generator (Tektronix FG502) creates a sinusoidal reference waveform used as input to a dual-op-amp (JFET TLO82CP) voltage-to-current converter 17 (VCC), which is powered by a Raytheon (864107-4) 25V power supply. The system is controlled with a National Instruments DAQCard 700 data acquisition card 15 (2.5 mV resolution) and a Compaq Presario 1700 notebook computer 16 with 256 MB of RAM with an 800 MHz processor. The acquisition software was written using National Instruments Lab Windows CVI 5.0 and was designed to continuously record the root mean square of voltage differential measurements, sampling at 12 kHz.

Sample Preparation

Male Wistar rats of 200 g were anesthetized and sacrificed. After ventral laparotomy, livers were excised and sliced using a scalpel, approximately 2.5 cm in length, 1–2 cm in width and 0.2–0.4 cm in thickness. Unless otherwise stated, experiments were conducted within 90 minutes from animal sacrifice with the tissue stored in 0.9% NaCl at room temperature until use. Size of sample, lag from time of sacrifice to data acquisition, and all voltage parameters were recorded for each sample. Liver tissue was chosen because it is macroscopically isotropic and, therefore, relatively homogenous, which minimizes any issues with the orientation of the electrodes with respect to the tissue. Also, there are no contractions during in vivo reversible electroporation with this organ, and at this stage it was preferable not to deal with corrections required for these contractions. Although only liver tissue was used for the experiments, other tissue samples could easily have been used with this device.

It also should be noted that the applied electroporation voltage-to-distance ratio in any experimental setup does not necessarily correlate with the electric field exposed to the tissue because of the voltage drop associated with the contact impedance between the electrode and the tissue. The voltage was applied across the entire length of the tissue, which should account for most of the voltage drop and, when necessary, electrocardiograph paste was applied between the tissue and the electrode to ensure good electrical contact. Therefore, we assume that this discrepancy is small and will use the terms interchangeably.

Experimental Results and Discussion

Initial Experiments with IQOFAS Pulses

Figure 2:
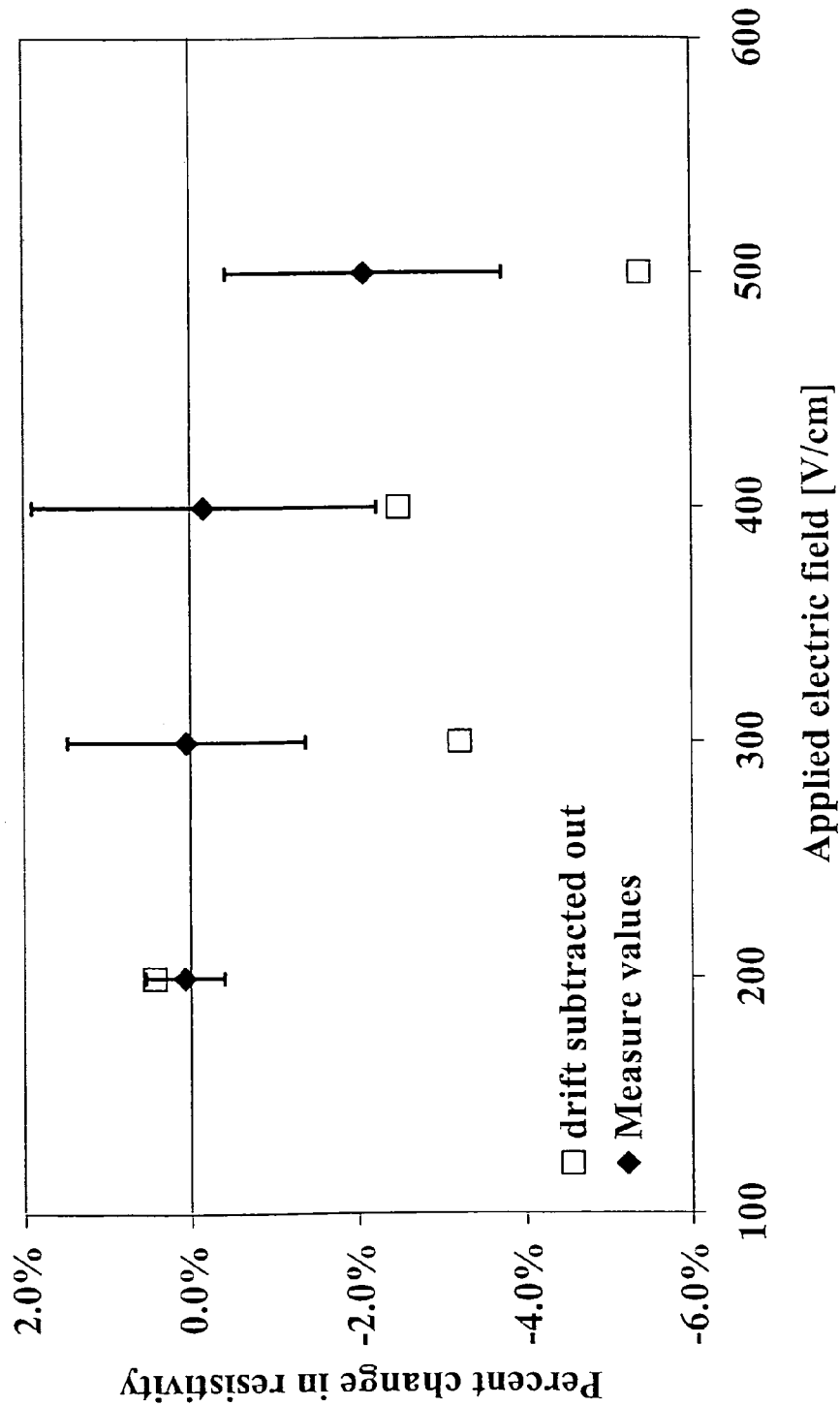
FIG. 2 is a graph of Applied electric field vs. percent change in resistivity.

Initial experiments were conducted using eight 100 us pulses at a frequency of 1 Hz with electric field varying from 0 to 500V/cm; these parameters are typical to ECT. The resistance of the tissue is calculated using Ohm's law by measuring the potential drop across the measuring electrodes and the current through the tissue (through the 2 kOhm resistor). These measurements are taken before and after delivery of the electroporation pulses. Since the electric pulse is applied across the entire tissue, the change in equivalent resistance corresponds to the change in resistivity. As shown in FIG. 2, the results are difficult to distinguish from signal drift and suggest conductivity changes less than 3%.

An index of the results is shown below in Table 6.1.

TABLE 6.1

Index of experimental results

| Figure | Pulse Length [ms] | Voltage Ratio [V/cm] | pulse number | Temperature [° C.] | Notes |
|---|---|---|---|---|---|
| 7 | .1 | 200–500 | 8 | 20 | — |
| 8 | 0.1–10 | 400 | 8 | 20 | — |
| 9 | 10 | 200–500 | 8 | 20 | — |
| 10 | 10 | 200–500 | 8 | 20 | Electrodes over portion of tissue |
| 11 | 10 | 200–500 | 8 | 20 | Transient Effects |
| 12 | 10 | 200–500 | 8 | 20 | Used in simulations |

Effect of Pulse Length on Normalized Conductivity Change

Figure 3:
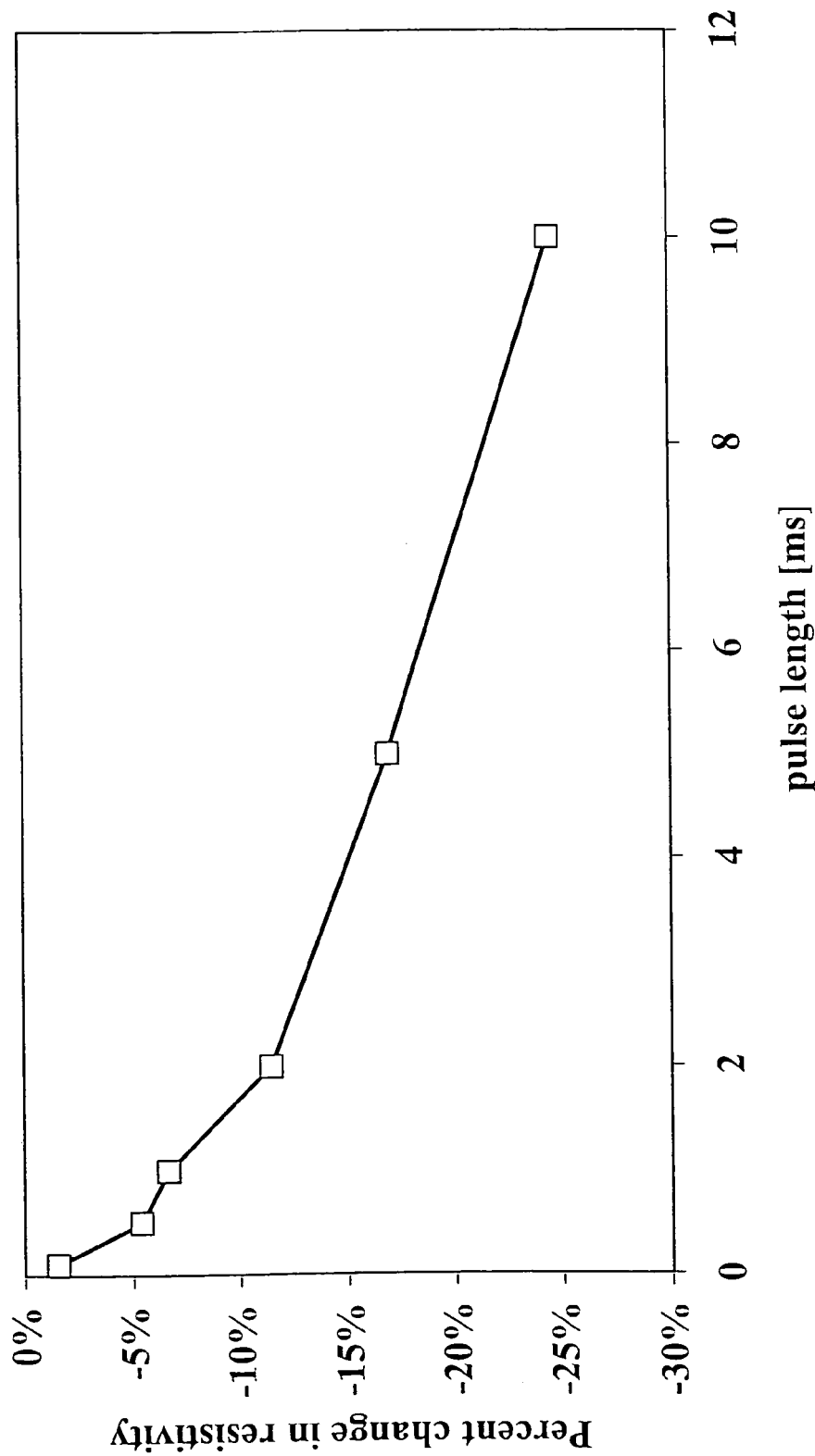
FIG. 3 is a graph of pulse length vs. percent charge in resistivity.
Figure 4:
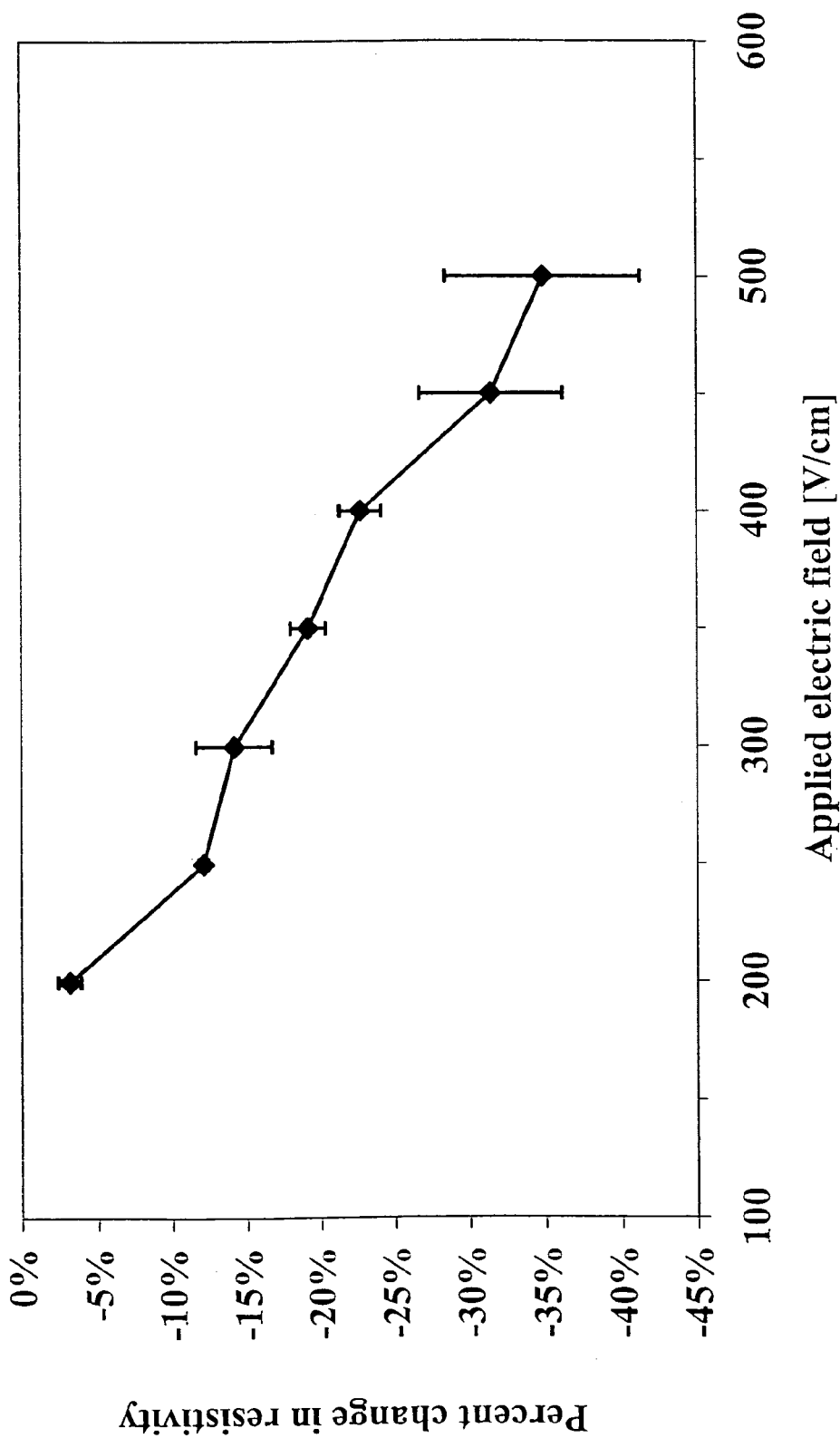
FIG. 4 is a graph of Applied electric field vs. percent change in resistivity.

The initial trials with 100 μs pulses of 100 microseconds showed only marginal conductivity changes of the tissue. Accordingly, the second set of experiments explored the effect of pulse length on conductivity change. Pulse length was varied from 100 microseconds to 10 milliseconds using eight 400V/cm pulses at I Hz while maintaining a constant voltage-to-distance ratio of 400V/cm. This limit was chosen because, under observation with the oscilloscope, the pulse shape began to loose integrity at lengths larger than 10 ms. FIG. 3 shows a strong dependence of conductivity change on pulse length and, at 10 ms, significantly larger changes in conductivity. FIG. 4 shows a drop in tissue resistivity for eight pulses at 100 Ohms at 1 Hz as a function of applied electric field

Experiments with 10 ms Pulses

Several experiments (2–5 per sample) were conducted using eight pulses at a frequency of IHz with a pulse length of 10 milliseconds. Dramatic changes were observed, which appeared to diminish over time. Since the time between the last pulse and the measurement was only accurate within a half second precision, the results are presented as a five second average, 10–15 seconds after the last pulse.

Experiments were conducted at 200(2), 250(2), 300(5), 350(2), 400(4), 450(3) and 500(3) V/cm, where the number in parenthesis is the number of trials at that gradient for a total of 32 experiments. The results showed an average drop in resistivity of 3.2±0.8 for 200 V/cm; 12.1±0.3 for 250 V/cm; 14.2.12.5 for 300 V/cm; 19.211.2 for 35 V/cm; 22.711.4 for 400 V/cm; 31.4+4.7 for 450 V/cm; and 34.8±6.5 for 500 V/cm. Standard deviation in the results was relatively small.

Electroporation Across a Percentage of the Tissue

Figure 5:
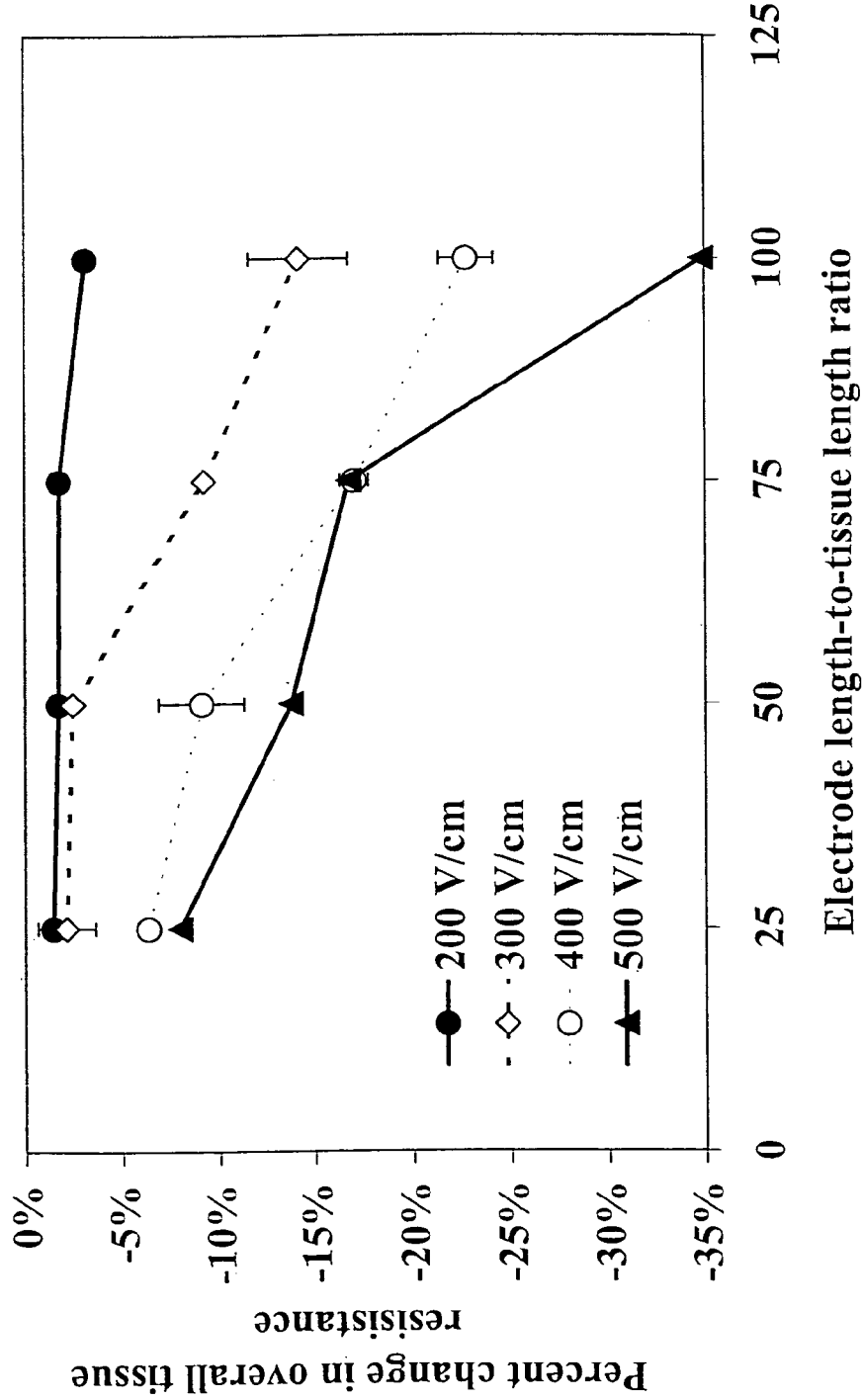
FIG. 5 is a graph of Electrical length-to-tissue length ratio vs. percent change in overall tissue resistance.
Figure 6:
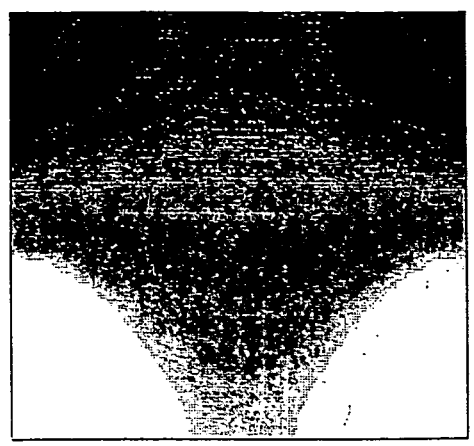
FIG. 6 is three images i, ii, and iii.
Figure 6:
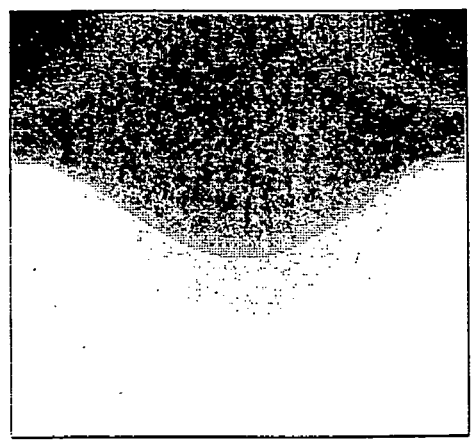
Figure 6:
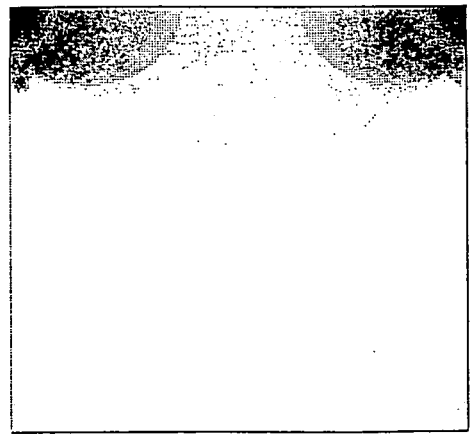

FIG. 5 shows the effects of varying the amount of tissue electroporated, rather than applying the electric across the entire length of the tissue. Electrodes were placed along 25%, 50%, 75% and 100% the width of the tissue. Two samples for each measurement was taken at 25%, 50% and 75% for 300V/cm and 400V/cm. FIG. 6 with frames i, ii and iii illustrates the setup as well as an analytical representation of the ensuing electrical field. A summary of these results are shown in FIG. 7.

Absolute Resistivity Measurement

With this set of experiments, resistance was recorded through the electroporation electrodes themselves. Measurements were taken by applying a IV pulse through these electrodes one second before the electroporation pulses and one second after. As mentioned earlier, this is generally not desirable in bioimpedance studies because the electrodes, which inject current, should not also be the measuring electrodes because of the induced uncertainty from the contact resistance.

This experiment made it possible to (1) estimate the absolute resistivity value of the tissue from the resistance measurement (because of the essentially rectangular geometry of the tissue samples); and (2) because no switching of the electrodes was required, measurements could be recorded within 1 s after the delivery of the final pulse.

Measurements were taken one second after the last electroporation pulse using the electroporation electrodes themselves, followed 15–20 s afterwards by the bioimpedance electrodes to explore transient effects. The results are summarized in FIG. 8.

Transient Effects

Figure 9:
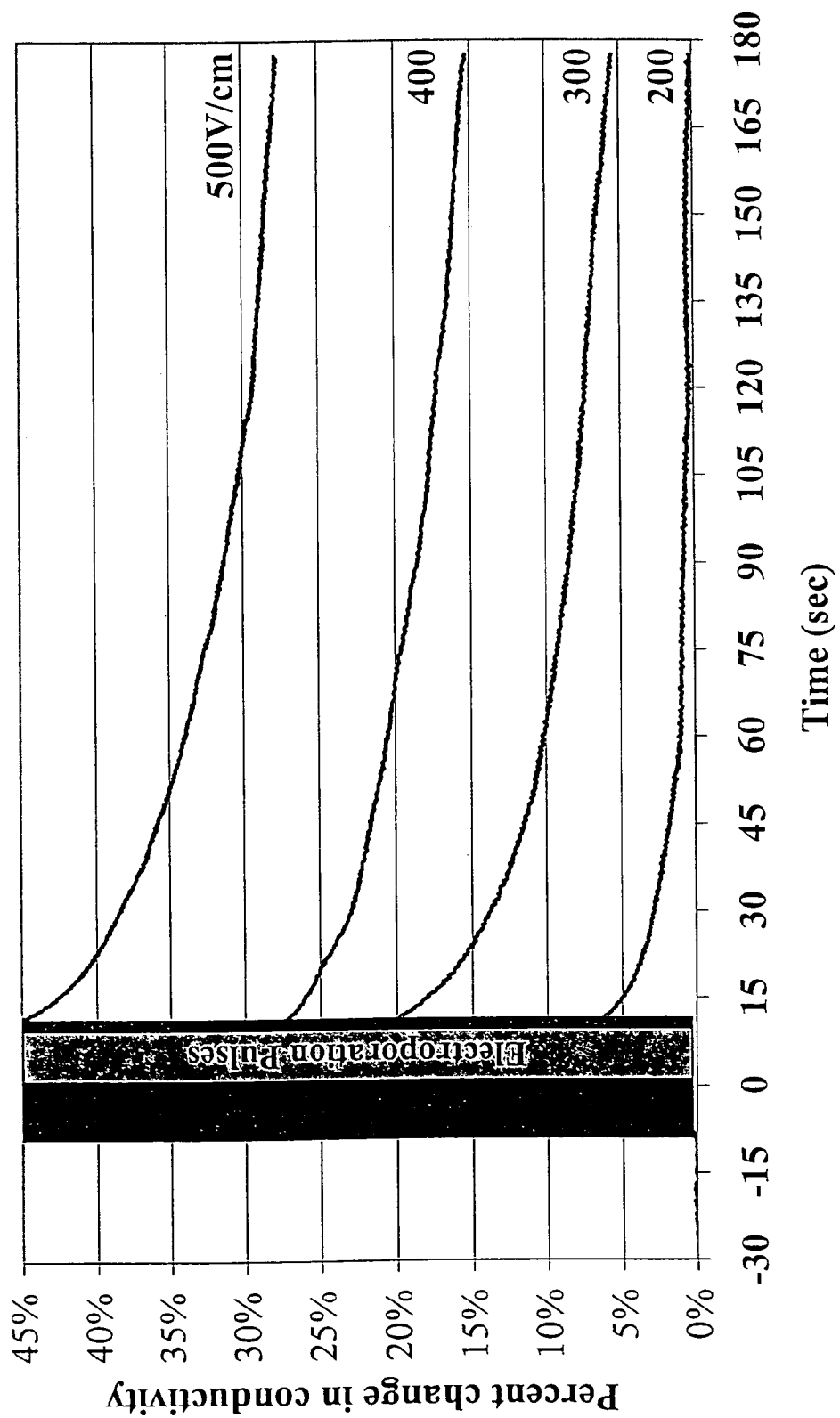
FIG. 9 is a graph of time vs. percent charge in conductivity.

Reversible electroporation is a transient phenomenon as shown above. The initial drop in resistance should eventually recover if the pulses are reversible. FIG. 9 plots the transient response of the conductivity change as a function of gradient. Since the electrodes used for measurement were stainless steel, polarization was inevitable. To compensate for this, the slope of the drift before electroporation was calculated and subtracted out from the overall response for each measurement. As the voltage gradient increased, the ability of the tissue to recover to its original conductivity decreased, resulting in an increasing residual conductivity change. This suggests the presence of both reversible and irreversible electroporation.

EXAMPLE

Numerical Method

A simplified two-dimensional isotropic cross-section of a liver 7 cm in diameter is used for the simulation. The surface of the analyzed tissue is assumed to be electrically isolated with a zero flux boundary condition to simulate a situation in which the liver is temporarily placed in an insulating, semi-rigid electrode array fixture during a surgical procedure. To collect data for the reconstruction algorithm, 32 electrodes are equally spaced around the periphery of the virtual phantom, i.e. electroporation conductivity map.

Experimental Results used in Front-Tracking Reconstruction Algorithm

For computational reasons and for model demonstration, we used the data from the 10 ms pulses in this study. Specifically, with these experiments, eight 10 ms pulses at a frequency of 1 Hz were delivered for electric fields of 0, 200, 300, 400 and 500V $cm^{-1}$. The threshold gradient required to induce electroporation was taken from the experimental data and was shown to be 200V $cm^{-1}$. The impedance change was measured with a 2.5 kHz, 0.3 mA rms sinusoidal current for 5 seconds, 10 seconds after the electroporation pulse. It was shown in earlier studies that permeability in tissues persists for periods longer than 15 seconds after delivery of the pulses. Three trials were performed for each gradient for a total of 15 experiments. These experimental results enable us to generate conductivity maps with five conductivity levels, including four degrees of electroporation in the tissue. A summary of the experimental results used as input into the electroporation models is included in FIG. 10.

Example 2

Electroporation Model

The electroporation simulation evaluates the potential and gradient distribution in the tissue due to an electrical pulse using the finite element method. To account for the change in electrical properties of the tissue during electroporation, the algorithm iteratively solves the Poisson equation with a zero source term:

$$\nabla \cdot (\sigma \nabla \phi) = 0$$

where $\sigma$ is the electrical conductivity and $\phi$ is the electrical potential. The conductivity of the tissue is assumed to be initially at 0.13 S m$^{-1}$, which agrees with results for dog liver in situ at 1kHz and measured from one sample. At locations where the voltage gradient surpasses a threshold gradient, the conductivity increases as prescribed by experimental results in FIG. 10. The gradients are recalculated with the updated conductivity values until the solution converges. For convergence, it was assumed that once the conductivity of an element increases, it will not revert to a lower value, at least within the duration of the data acquisition. This result is used to generate a conductivity map with five conductivity levels, including four degrees of electroporation in the tissue. The BIT simulation reconstructs an image of the electroporated area using the conductivity map as a virtual phantom.

Example 3

Ex Vivo Reconstruction Examples

In addition to the baseline example, three electroporation electrode geometrical configurations were investigated, which are modeled after in vivo electroporation experiments conducted on rabbit liver and murine skeletal muscle.

Figure 11:
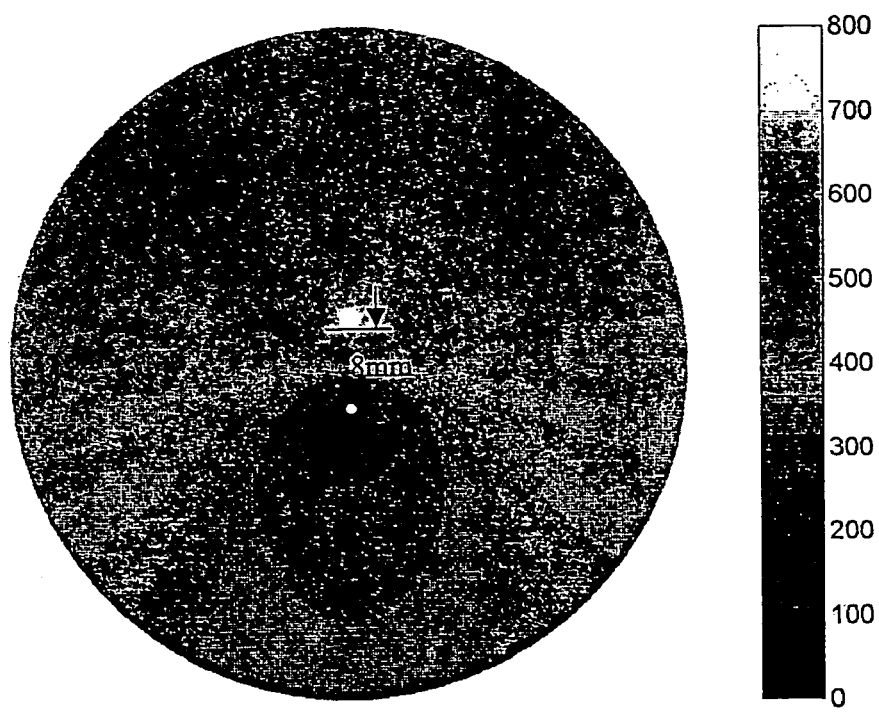
FIG. 11 is an image of potential distribution.

The first configuration which is show in FIG. 11 had two electrodes separated with an inner distance of 8 mm, centered in the liver, with one electrode at 800V and the other grounded. The second configuration was similar to the first, except that the applied voltage was 600V. The third configuration had two rows of four electrodes centered in the liver. The center-to-center distance between the two rows was 4 mm, and the center-to-center spacing between the electrodes in each row was 2 mm. The voltage of the top row was set to 1200V and the bottom row to ground. The diameters of the electrodes for the two examples were 1.1mm, 0.3 mm, and 0.5 mm, respectively.

Example 4

Numerical Results

Reconstruction Model

The reconstruction algorithm consisted of a 116-element mesh with 96 peripheral elements and 20 elements defining the electroporated area. The outer region maintained a conductivity of 0.13 S/m while the inner region used a weighted conductivity value of 0.2 S/m. The algorithm initially assumes the electroporated region to be a circle with a 6 mm radius centered between the electroporation electrodes. The boundary conditions were zero flux for periphery segments except for the electrode source and sink. The BIT electrode element widths were 1 mm, and the source/sink current was +/−1 mA.

Example 5

Reconstruction Examples

Figure 12:
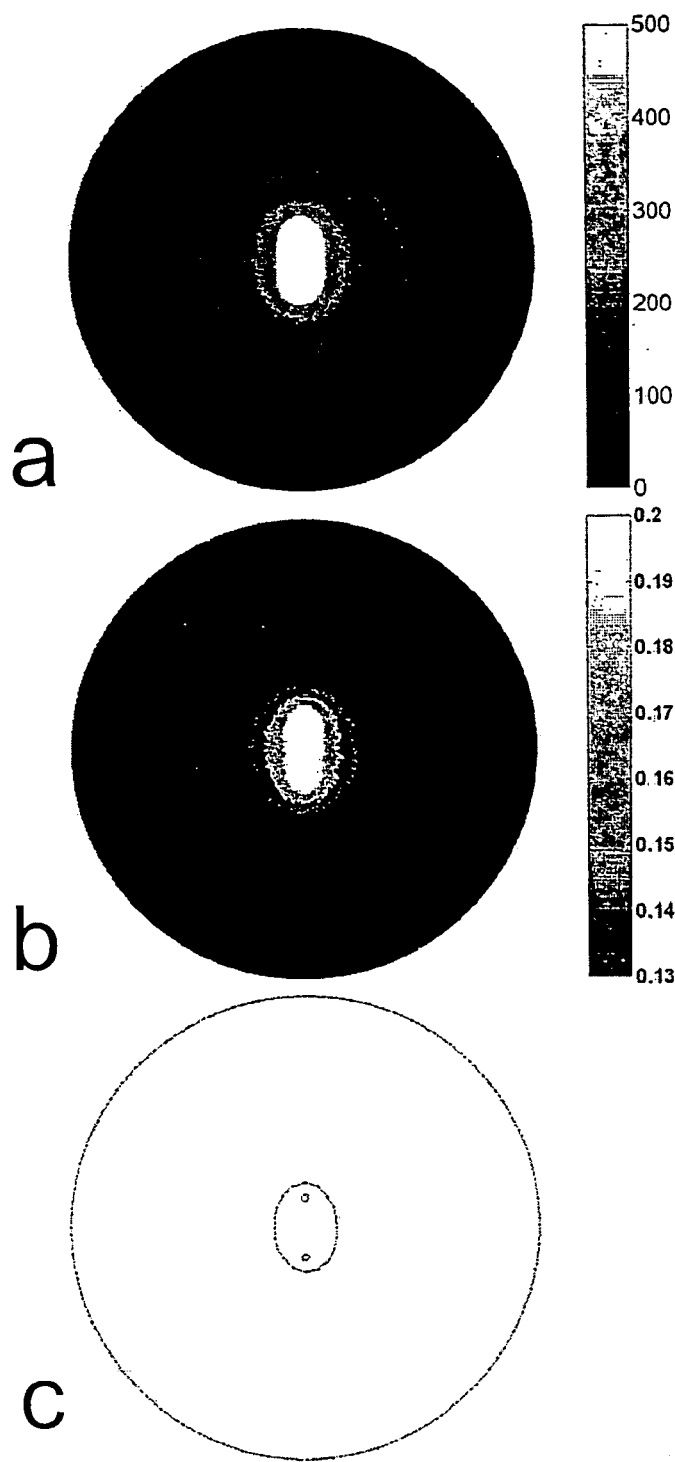
FIG. 12 is three images of electric field distribution.

FIG. 11 shows the potential distribution and labels the relevant dimensions and boundary conditions for the first configuration. FIGS. 12a, 12b and 12c depict selected modeling and imaging steps in our simulation for this configuration. FIG. 12a shows the converged solution for the gradient distribution. For elements above a threshold gradient, the conductivity was increased to our measured value. FIG. 12b shows the conductivity map generated using the information from FIG. 12a. This distribution is then passed to the EIT imaging module, and FIG. 12c shows the generated image.

Figure 13:
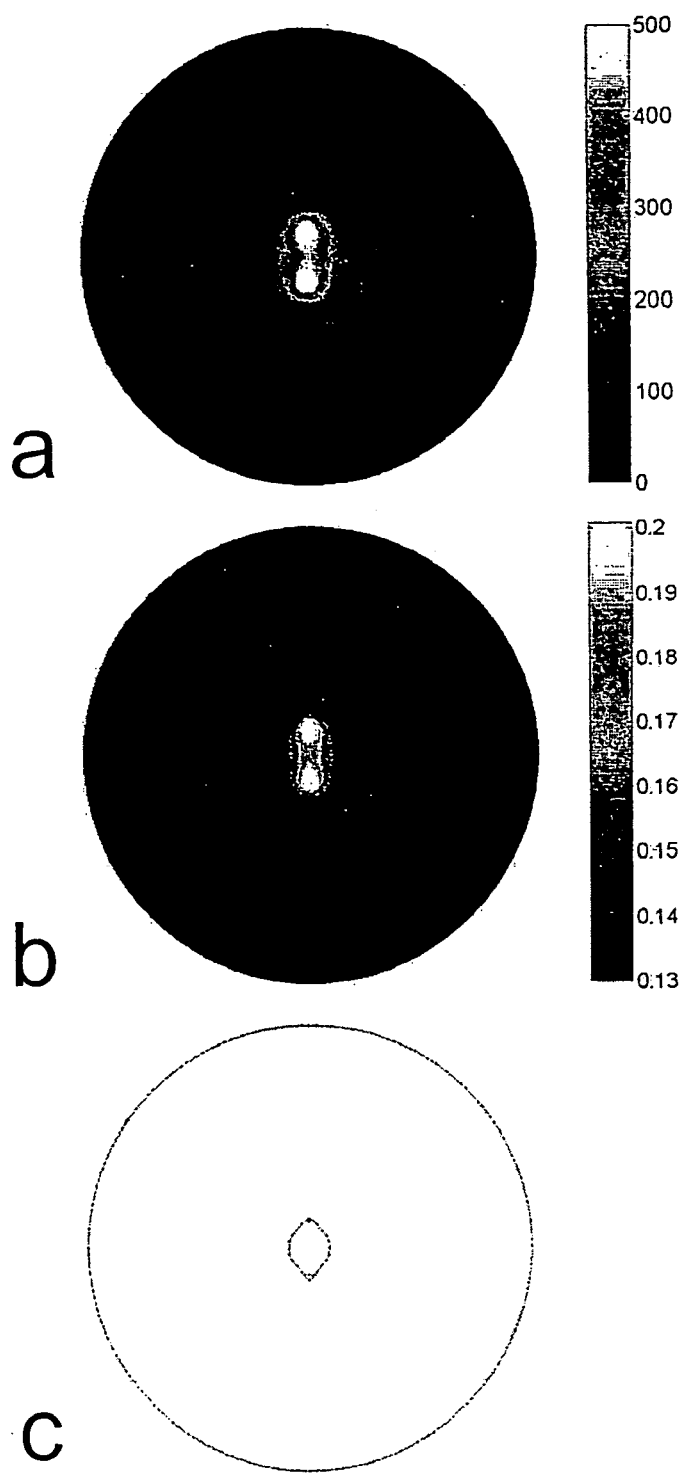
FIG. 13 is three images of electric field distribution.
Figure 14:
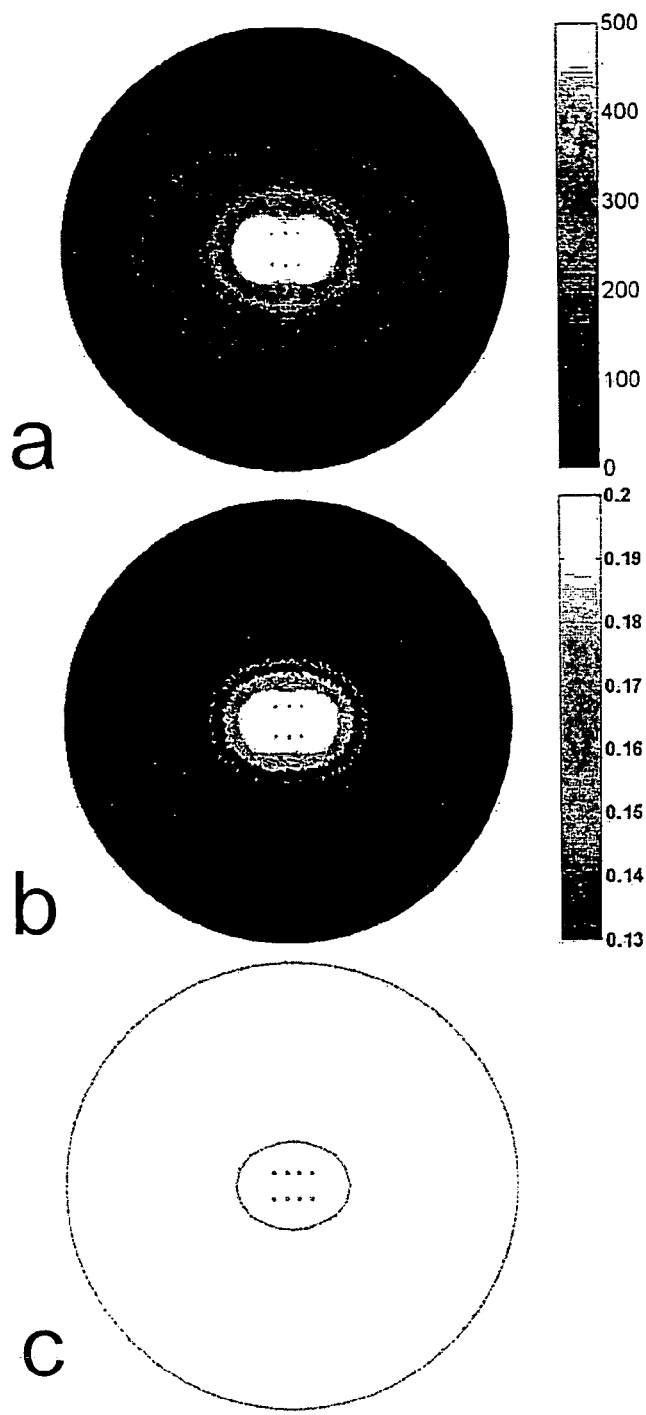
FIG. 14 is three images of electric field distribution.

FIGS. 13a, 13b and 13c show the gradient distribution, conductivity map, and the generated image for the second example, respectively. FIGS. 14a, 14b and 14c show the gradient distribution, conductivity map, and the generated image for the third example, respectively. For the three configurations, no quantitative discernability studies were performed, but a noticeable decrease in image quality was observed as noise levels approached 5.0% of the maximum measured BIT voltage amplitude.

Example 6

Baseline Example

Figure 10:
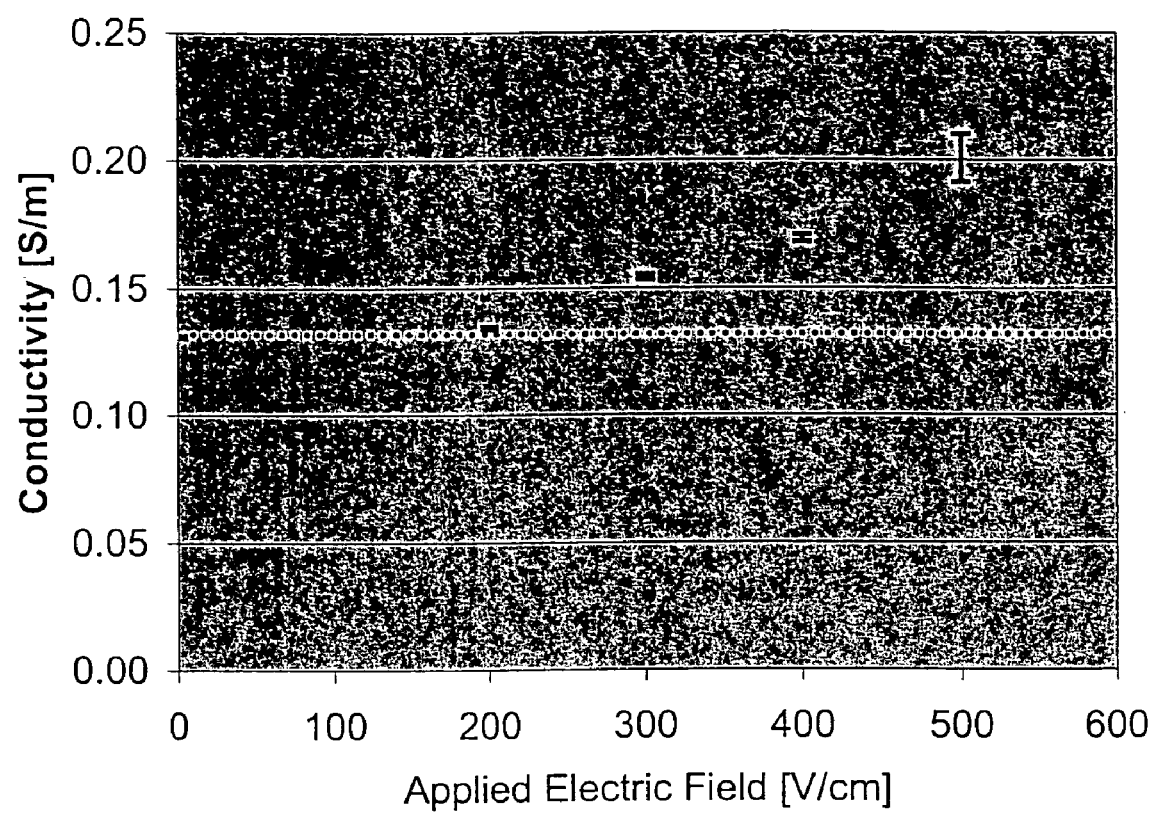
FIG. 10 is a graph of conductivity vs. applied electric field.

FIGS. 15a and 15b show the conductivity map and the reconstructed image for a baseline example using biological properties updated from the ex vivo experimental data presented in FIG. 10. This example uses 16 BIT electrodes with an imaging domain of 10 cm. There were four electroporation electrodes located in the center of the tissue with the top electrodes set to 1300V and the bottom electrodes set to ground. The number of periphery elements used in this example was 64.

Parametric Studies

The variables used by the reconstruction algorithm, namely 1) the number of elements defining the electroporated area, 2) the conductivity of the inner region, 3) the initial radius of the inner region, 4) the domain size, and 5) the number of HIT electrodes, were studied parametrically. The parameters from the first three examples were used as control using the electroporation electrode configuration from the baseline model. The control model used in the reconstruction algorithm consisted of a 180-element mesh with 160 peripheral elements and 20 elements defining the electroporated area. The inner region had a conductivity value of 0.2 S/m and was initially assumed to be a circle with a 6 mm radius centered between the electroporation electrodes. There were four electroporation electrodes located in the center of the tissue placed in a square configuration, 10 mm from one another, with the top electrodes set to 1300V and the bottom electrodes set to ground.

Figure 16:
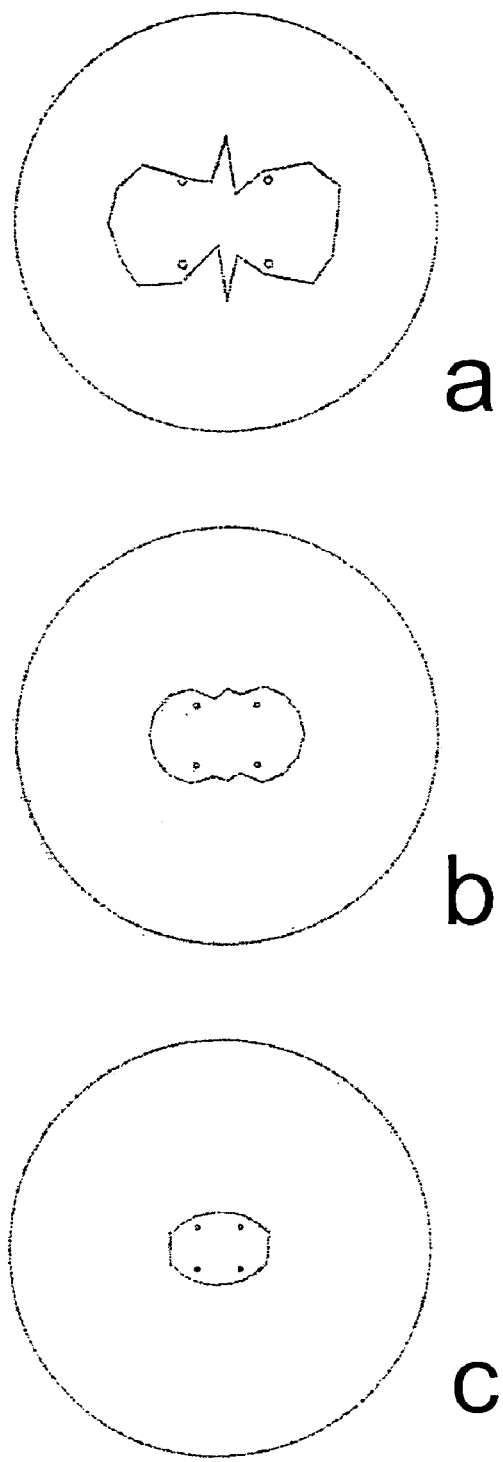
FIG. 16 is three images of electric field distribution.
Figure 17:
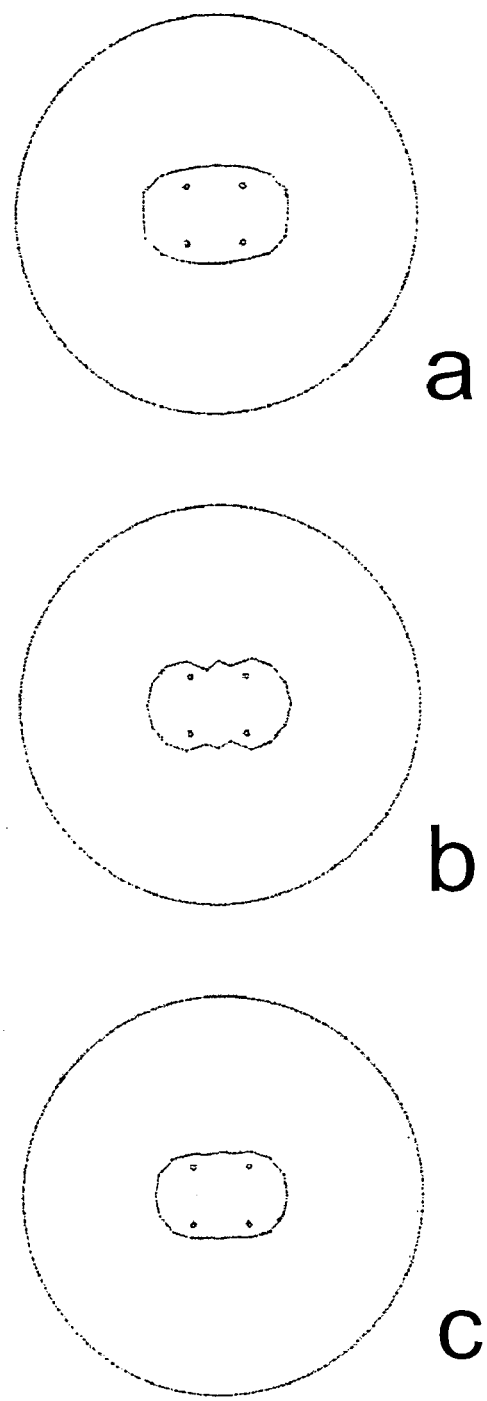
FIG. 17 is three images of electric field distribution.
Figure 18:
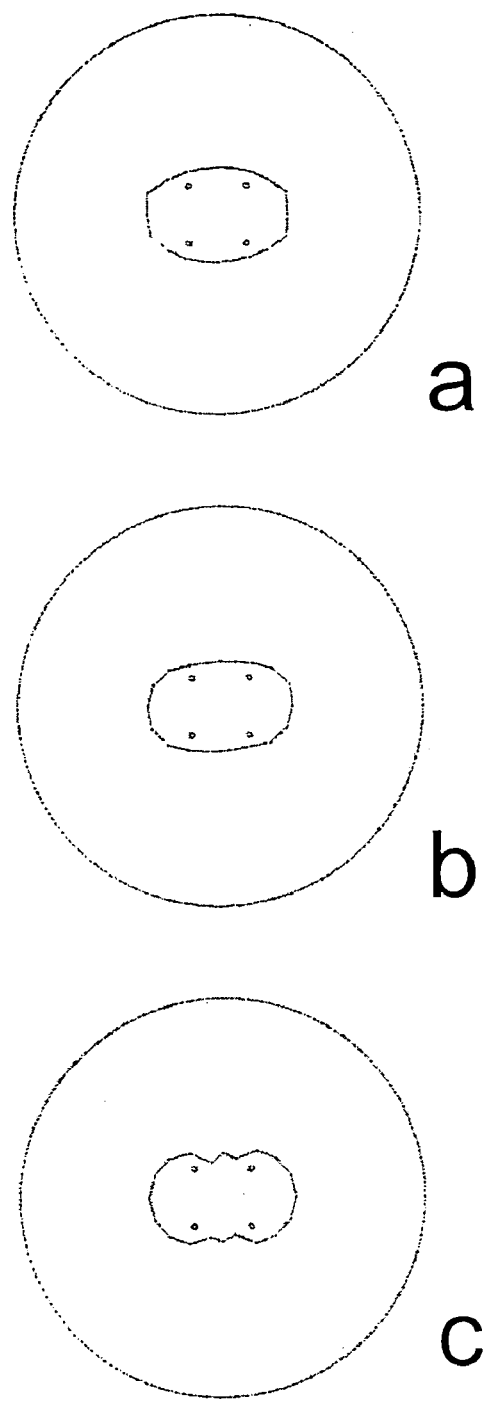
FIG. 18 is three images of electric field distribution.
Figure 19:
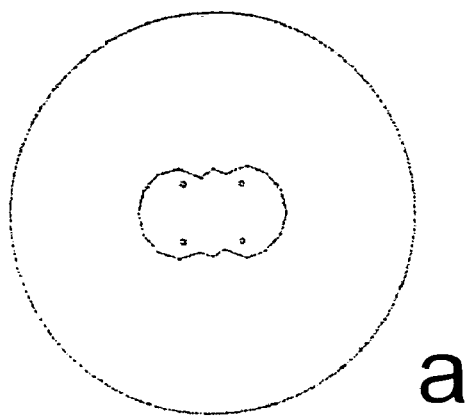
FIG. 19 is three images of electric field distribution.
Figure 19:
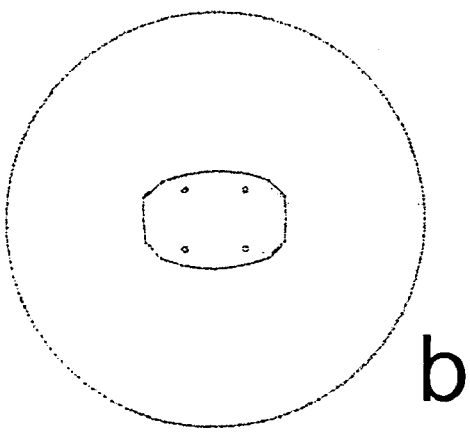
Figure 19:
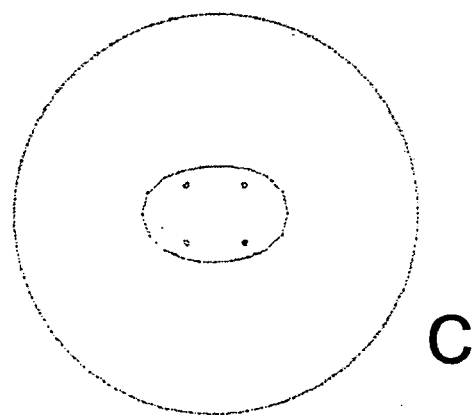
Figure 20:
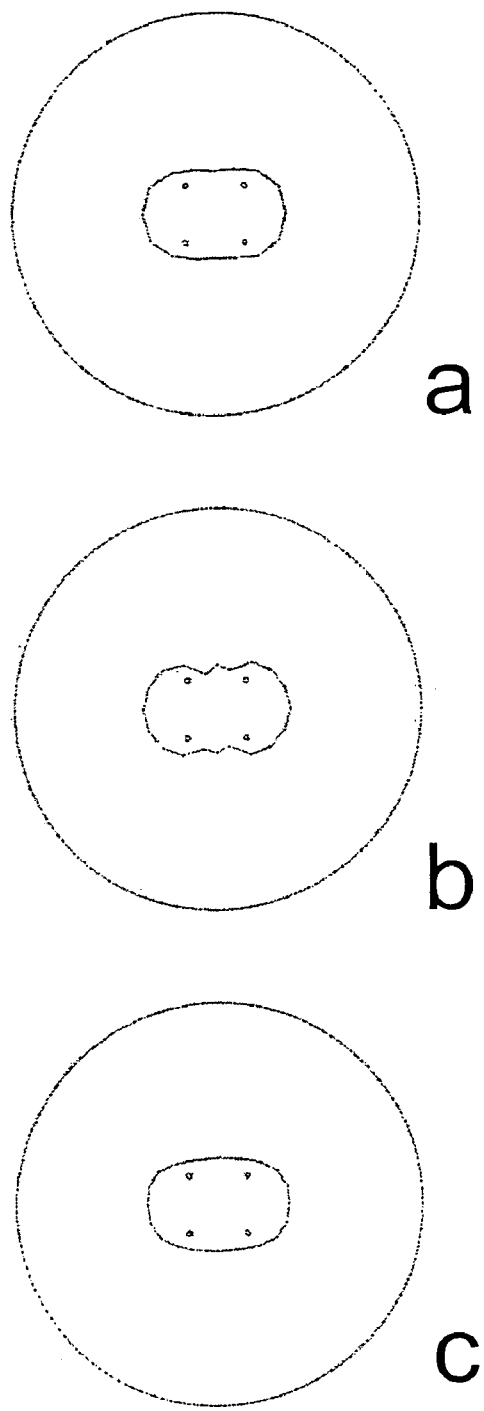
FIG. 20 is three images of electric field distribution.

FIGS. 16a, 16b and 16c show the effect that the size of the surrounding region had on the reconstructed image for region diameters of 25 cm, 35 cm and 50 cm, respectively. FIGS. 17a, 17b and 17c show the reconstructed image for inner conductivity values of 0.19 S/m, 0.20 S/m and 0.21 S/m, respectively. FIGS. 18a, 18b and 18c show the reconstructed image using 16, 24 and 32 surrounding EIT electrodes, respectively. It should be noted that the number of periphery elements for these three examples was 80, 120 and 160, respectively. FIGS. 19a, 19b and 19c show reconstructed images using initial inner region radiuses of 6, 8 and 10 mm, respectively. FIGS. 20a, 20b and 20c show the reconstructed image using 18, 20 and 22 elements to define the electroporated area, respectively.

Discussion

There are two primary applications for in vivo electroporation: antitumor electrochemotherapy (ECT) and electrotransfer as a novel approach of non-viral gene therapy. Lower field strengths with long pulses are generally used, in addition to permeabilizing the membrane, to electrophoretically push the macromolecules into the cell. This is not required for small drugs such as bleomycin, which enter a permeabilized cell via diffusion. For example, the protocols for porcine skeletal muscle are 450V/cm with 100 us pulses for ECT but only 90V/cm with 20 ms pulses for gene therapy.

Initial trials with 100μs pulses suggested conductivity changes of less than 3%. With 10 ms pulses, at 10 ms, significantly larger changes in conductivity were observed.

As the voltage gradient increased, the ability of the tissue to recover to its original conductivity decreased, resulting in an increasing residual conductivity change. This suggests the presence of both reversible and irreversible electroporation. Furthermore, these results also show that EIT monitoring to be more applicable for applications requiring longer pulses such as gene therapy, which inherently needs more precision than ECT. Because the conductivity change is essentially permanent and more significant for irreversible electroporation, these results also show that EIT is suitable to image irreversible electroporation.

The results in FIGS. 12–15, obtained using realistic experimental data, demonstrate that EIT can produce an image of the area affected by electroporation. The three examples were placed in the center of the tissue because this is the most difficult location to image because conductivity perturbations at this location would minimally affect the surface voltage measurements. It should be noted that the examples in the previous chapters used a more dramatic change in conductivity, but a smaller imaging region than the ones presented here, and only 16 peripheral electrodes as opposed to 32. The reconstruction algorithm produced excellent images of the first and third examples but was only able to reconstruct the general location and not the shape of the image of the second example.

The second example is difficult to image as the reconstruction algorithm currently is written. This is because of its convex shape and two local maxima, i.e. two separate regions with 500V/cm thresholds centered at each electrode. This problem should be resolvable with future iterations of the algorithm. The other examples had concentric conductivity regions, which is much easier to image with one average conductivity value.

To image example 2 appropriately, the algorithm can be written to incorporate multiple embedded conductivity regions.

Examples may derive the electroporated tissue conductivity from in vitro cell experimental results taken while the pulse was applied. If the transient ex vivo experimental results presented above and in FIGS. 1–20 are extrapolated to the instant the pulse was removed, the results are comparable. This shows that it would be ideal if the bioimpedance measurement could occur during the application of the pulse; however, the relatively short duration of an electroporation pulse makes this difficult.

Figure 15:
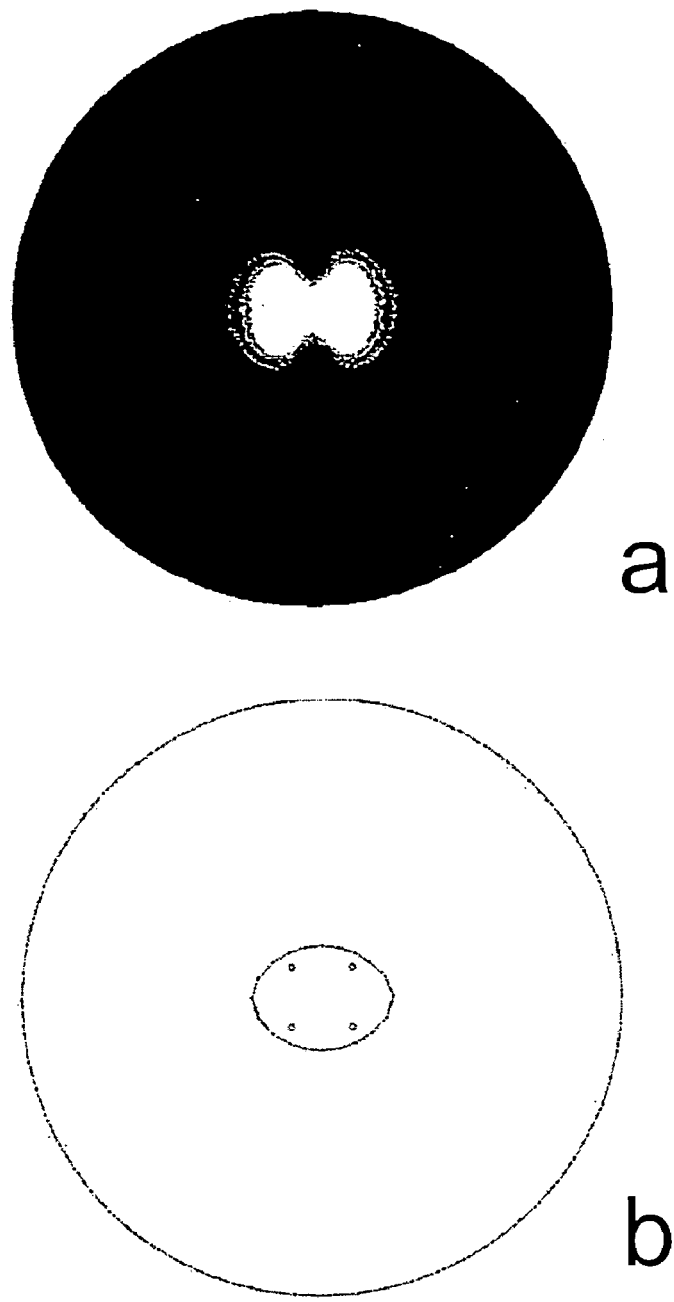
FIG. 15 is two images of electric field distribution.

The results in FIG. 15 show that the baseline reconstruction example is still reproducible with less dramatic and multi-level conductivity perturbations. General parameters, such as domain size and number of imaging electrodes, as well as parameters specific to this reconstruction algorithm, such as the number of elements defining the electroporated area, the conductivity of the inner region, and the initial radius of the inner region, could be changed to determine effects on the ability of the algorithm to produce an accurate image. The effects of these variables were explored using the electroporation electrode configuration in the baseline model and the geometrical configuration in the examples presented above. The results in FIGS. 16–20 show that the number of imaging electrodes and the imaging domain, surprisingly, only marginally affect the image. The parameters that most affect the image are inherent to the algorithm itself. This shows that preemptive care must be taken in choosing these parameters appropriately and future studies must be done to optimize them. The advantage of having the algorithm parameters dominate the image reconstruction as opposed to the physical system parameters, is that it provides complete control over these variables and they are not dictated by the surgical procedure.

CONCLUSION

In summary, with electroporation, as in all other molecular medicine techniques, there is no method to actively monitor or control the process in real-time, i.e., to determine during the procedure that the cell membranes have become temporarily permeabilized in the desired area of the tissue. However, the above Examples demonstrate that monitoring of molecular medicine in vivo can be achieved through the synthesis of two fairly well understood techniques, electroporation and BIT.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method for performing electroporation in a controlled manner, comprising:
    (a) applying a voltage across a tissue comprising a plurality of biological cells;
    (b) continuously detecting the ratio of electric current through the tissue to voltage across the tissue as an indication of degree of electroporation of the biological cells; and
    (c) adjusting the applied voltage in accordance with changes in current-to-voltage ratio to achieve a controlled degree of electroporation averaged over the biological cells, thereby achieving a controlled averaged degree of electroporation of the biological cells in the tissue.

2. The method of claim 1, wherein:
    step (b) comprises continuously detecting the current-to-voltage ratio as an indication of an onset of electroporation of the biological cells, and
    step (c) comprises adjusting duration of the applied voltage in accordance with the current-to-voltage ratio to achieve a controlled degree of electroporation.

3. The method of claim 1, wherein:
voltage is applied between two electrodes in a flow-through channel, and the electrodes are positioned to apply voltage in a direction transverse to a direction of flow through the channel;
  step (a) comprises continuously passing the tissue through the channel;
  step (b) comprises further correlating the current-to-voltage ratio with the presence of the biological cell between the electrodes; and
  step (c) comprises adjusting the magnitude of the voltage while the biological cells are between the electrodes based on an averaged degree of electroporation of the biological cells in the tissue.

4. A method for the infusion of biological cells in a tissue with a chemical substance by electroporation in a manner that permits detection of onset of and control of the electroporation, comprising:
  (a) securing biological cells in the tissue in an electrical cell containing a liquid with the chemical substance dissolved therein, the electrical cell containing a barrier to electric current, the barrier arranged such that, when a voltage is imposed across the electrical cell, the barrier restricts electric current flow to a flowpath passing through the biological cells while permitting substantially no electric current to bypass the biological cells in the tissue;
  (b) imposing a voltage across the electrical cell and monitoring relative values of current passing through the electrical cell and of imposed voltage as an indication of occurrence of electroporation of biological cells in the tissue.

5. The method of claim 4, wherein the barrier divides first and second electrode chambers in the electrical cell and contains an opening smaller in width than a grouping of biological cells, and (a) comprises securing the grouping of biological cells over an opening such that grouping of cells closes the opening.

6. The method of claim 5, wherein the first electrode chamber contains a first electrically conducting liquid and the second electrode chamber contains a second electrically conducting liquid, and the chemical substance is dissolved in only one of the first and second electrically conducting liquids.

7. The method of claim 5, wherein the first electrode chamber contains a first electrically conducting liquid and the second electrode chamber contains a second electrically conducting liquid, and the chemical substance is dissolved in both of the first and second electrically conducting liquids.

8. The method of claim 5, wherein step (a) is accomplished by imposing a pressure differential across the opening to press the grouping of biological cells against one side of the opening.

9. The method of claim 5, wherein step (a) is accomplished using a coating on an area surrounding the opening, the coating comprised of a substance that binds to the barrier.

10. The method of claim 5, wherein the first electrode chamber is constructed and arranged to permit continuous flow of liquid therethrough, the method further comprising effecting continuous flow of a first electrically conducting liquid through the first electrode chamber.

11. The method of claim 5, wherein the first and second electrode chambers are constructed and arranged to permit continuous flow of liquid through each such chamber independently, the method further comprising effecting continuous flow of a first electrically conducting liquid through the first electrode chamber and continuous flow of a second electrically conducting liquid through the second electrode chamber.

12. The method of claim 4, wherein the electric cell is transparent, and the method further comprises observing changes in the grouping of biological cells while the voltage is imposed.

13. A device for the infusion of a grouping of biological cells of a tissue with a chemical substance by electroporation, comprising:
  an electric cell containing an internal support to hold a grouping of biological cells of a tissue and an internal barrier of a material substantially impermeable to electric current, the baffler positioned to restrict electric current flow in the electric cell to a flowpath crossing the internal support and through biological cells held thereby; and
  means for imposing a voltage across the electric cell and for monitoring relative values of current and voltage as an indication of occurrence and degree of electroporation in biological cells held thereby.

14. The device of claim 13, wherein the baffler divides the interior of the electric cell into first and second electrode chambers and the internal support is an opening in the baffler smaller in width than a biological cell.

15. The device of claim 13, further comprising a means for imposing a pressure differential across the opening to lodge the grouping of biological cells in the opening.

16. A method, comprising:
  (a) identifying a grouping of biological cells in a tissue of a living mammal and applying a voltage across the cells;
  (b) continuously detecting a ratio of electric current through the cells to voltage across the cells as an indication of degree of electroporation of the biological cells; and
  (c) adjusting a determined magnitude of the applied voltage in accordance with changes in detected magnitude of the current-to-voltage ratio to achieve a controlled degree of electroporation of the grouping of cells in the tissue.

17. The method of claim 16, wherein step (b) comprises continuously detecting the current-to-voltage ratio in an indication of onset of electroporation of biological cells, and step (c) comprises adjusting the duration of the applied voltage in accordance with continuously detected current-to-voltage ratio to achieve a controlled degree of electroporation of the grouping of cells in the tissue.

18. The method of claim 16, wherein the current-to-voltage ratio is an indication of degree of electroporation averaged over cells of the grouping of biological cells, achieving a controlled averaged degree of electroporation of the grouping of biological cells.

19. The method of claim 16, wherein the voltage is applied between two microelectrodes positioned with the grouping of biological cells in between.

20. A method, comprising:
  (a) placing biological tissue in an electrically conductive medium and applying a voltage across the medium;
  (b) continuously detecting the ratio of electric current through the medium to voltage across the medium as an indication of degree of electroporation of cells of the biological tissue; and
  (c) adjusting a magnitude of the applied voltage in accordance with changes in magnitude of the current-to-voltage ratio to achieve a controlled degree of electroporation of cells of the biological tissue.

* * * * *